United States Patent
Mukkamala et al.

(10) Patent No.: US 12,011,297 B2
(45) Date of Patent: Jun. 18, 2024

(54) MOBILE DEVICE APPLICATIONS TO MEASURE BLOOD PRESSURE

(71) Applicant: BOARD OF TRUSTEES OF MICHIGAN STATE UNIVERSITY, East Lansing, MI (US)

(72) Inventors: Ramakrishna Mukkamala, Okemos, MI (US); Anand Chandrasekhar, East Lansing, MI (US); Keerthana Natarajan, East Lansing, MI (US); Mohammad Yavarimanesh, Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 713 days.

(21) Appl. No.: 17/256,609

(22) PCT Filed: Jun. 28, 2019

(86) PCT No.: PCT/US2019/039997
§ 371 (c)(1),
(2) Date: Dec. 28, 2020

(87) PCT Pub. No.: WO2020/006518
PCT Pub. Date: Jan. 2, 2020

(65) Prior Publication Data
US 2021/0267550 A1 Sep. 2, 2021

Related U.S. Application Data

(60) Provisional application No. 62/724,461, filed on Aug. 29, 2018, provisional application No. 62/691,472, filed on Jun. 28, 2018.

(51) Int. Cl.
*A61B 5/00* (2006.01)
*A61B 5/022* (2006.01)
(Continued)

(52) U.S. Cl.
CPC ........ *A61B 5/6898* (2013.01); *A61B 5/02225* (2013.01); *A61B 5/0295* (2013.01);
(Continued)

(58) Field of Classification Search
CPC . A61B 5/6898; A61B 5/02225; A61B 5/0295; A61B 5/1075; A61B 5/743;
(Continued)

(56) References Cited

U.S. PATENT DOCUMENTS 9,851,800 B1 * 12/2017 Kneisley ................. G06F 3/017
2008/0086533 A1 * 4/2008 Neuhauser ............. A61B 7/003
709/224
(Continued)

FOREIGN PATENT DOCUMENTS

WO 2012099535 A1 7/2012
WO 2017152098 A1 9/2017

OTHER PUBLICATIONS

ISO 81060-2:2018—Non-Invasive Sphygmomanometers—Part 2: Clinical Investigation of Intermittent Automated Measurement Type, Nov. 2018, 6 pages [only informative sections of standards].
(Continued)

*Primary Examiner* — Sean D Mattson
(74) *Attorney, Agent, or Firm* — Quarles & Brady LLP

(57) ABSTRACT

Various systems, techniques, and embodiments are disclosed for implementing a blood-pressure measurement method that does not require specialized equipment (such as inflatable blood pressure cuffs). The measurement can be taken from arterial locations within a user's finger, via the standard equipment and features of many widely-available consumer mobile devices. Such devices can be programmed to accurately and easily guide a user to press her finger on the screen of a device at a precise location, so that an accurate measurement can be taken. For example, guidance visual-
(Continued)

izations on a screen (such as finger silhouettes and animations) can be employed on the same screen on which a user presses her finger. Pressure sensitivity and optical camera readings are then used to calculate blood pressure for the user.

29 Claims, 16 Drawing Sheets

(51) Int. Cl.
*A61B 5/0295* (2006.01)
*A61B 5/107* (2006.01)
*G06F 3/044* (2006.01)
*H04W 88/02* (2009.01)

(52) U.S. Cl.
CPC ............ *A61B 5/1075* (2013.01); *A61B 5/743* (2013.01); *G06F 3/044* (2013.01); *A61B 2562/0247* (2013.01); *A61B 2562/0261* (2013.01); *H04W 88/02* (2013.01)

(58) Field of Classification Search
CPC ... A61B 5/6887; A61B 5/0022; A61B 5/7278; A61B 2562/0247; A61B 2562/0261; A61B 2562/0233; A61B 2562/146; A61B 2562/227; A61B 2560/0462; A61B 2560/0223; A61B 2503/10; G06F 3/044; H04W 88/02; G16H 40/67
See application file for complete search history.

(56) References Cited

U.S. PATENT DOCUMENTS

| | | | |
|---|---|---|---|
| 2012/0190944 A1* | 7/2012 | Thaveeprungsriporn | ................... A61B 5/1455 600/310 |
| 2014/0135594 A1 | 5/2014 | Yuen et al. | |
| 2015/0062078 A1 | 3/2015 | Christman et al. | |
| 2017/0079591 A1 | 3/2017 | Gruhlke et al. | |
| 2017/0251935 A1 | 9/2017 | Yuen | |
| 2017/0354332 A1* | 12/2017 | Lamego | ................ A61B 5/6898 |
| 2018/0067600 A1* | 3/2018 | Li | ............................ G01L 25/00 |
| 2018/0173343 A1 | 6/2018 | Pi et al. | |
| 2018/0303351 A1 | 10/2018 | Mestha et al. | |
| 2019/0357779 A1* | 11/2019 | Park | ................... A61B 5/02241 |
| 2020/0196881 A1* | 6/2020 | Zemel | ................ A61B 5/02444 |

OTHER PUBLICATIONS

Air Measure, Measure Anything. Anywhere., http://armeasure.com/, Accessed Aug. 24, 2018, 8 pages.
Google Play, Moasure—The Sman Tape Measure, 3D Technologies, https://play.google.com/store/apps/details?id=com.Moasure.Moasure&hl=en_US, Dec. 23, 2020, 4 pages
YouTube, Huawei Mate S force Touch Demo [english], Sep. 2, 2015, https://www.youtube.com/watch?v=ta6beOvyhYE, 5 pages.
PCT International Search Report and Written Opinion, PCT/US2019/039997, Sep. 24, 2019, 15 pages.
European Patent Office, Extended Search Report, Application No. 19826337.8, Mar. 11, 2022, 10 pages.
Agarwal et al., Role of Home Blood Pressure Monitoring in Overcoming Therapeutic Inertia and Improving Hypertension Control: A Systematic Review and Meta-Analysis, Hypertension, 2011, 57:29-38.
Alpert et al., Oscillometric Blood Pressure: A Review for Clinicians, Journal of the American Society of Hypertension, 2014, 8(12):930-938.
Bastawrous et al., Mobile Health Use in Low- and High-Income Countries: An Overview of the Peer-Reviewed Literature, Journal of the Royal Society of Medicine, 2013, 106(4):130-142.
Beulen et al., Toward Noninvasive Blood Pressure Assessment in Arteries by Using Ultrasound, Ultrasound in Medicine & Biology, 2011, 37(5):788-797.
Cappelli et al., Fingerprint Image Reconstruction from Standard Templates, IEEE Transactions on Pattern Analysis and Machine Intelligence, 2007, 29(9):1489-1503.
Carson et al., In-Screen Fingerprint Sensors Coming to 100 Million Phones by 2019, https://www.cnet.com/news/in-screen-fingerprint-sensors-coming-to-100-million-phones-by-2019-report/, Apr. 26, 2018, 5 pages.
Chamary, 3D Touch in iPhone 6S Isn't Just a Gimmick. Here's How It Works, https://www.forbes.com/sites/ivchamary/2015/09/12/3d-touch-iphone-6s/# 30f4fdd44cee, Sep. 12, 2015, 6 pages.
Chandrasekhar et al., Smartphone-Based Blood Pressure Monitoring via the Oscillometric Finger-Pressing Method, Science Translational Medicine, 2018, 10(431), 24 pages.
Chandrasekhar et al., An iPhone Application for Blood Pressure Monitoring via the Oscillometric Finger Pressing Method, Scientific Reports, 2018, 8:13136, pp. 1-6.
Chockalingam, Impact of World Hypertension Day, Can. J. Cardiol., 2007, 23(7):517-519.
Colak et al., Blood Pressure Estimation Using Neural Networks, In 2004 IEEE International Conference on Computational Intelligence for Measurement Systems and Applications, pp. 21-25.
Draper et al., Chapter 14, "Dummy" Variables, in Applied Regression Analysis, 3rd Edition, 1998, pp. 299-325.
Drzewiecki et al., Theory of the Oscillometric Maximum and the Systolic and Diastolic Detection Ratios, Annals of Biomedical Engineering, 1994, 22(1):88-96.
Drzewiecki, Chapter 55, Noninvasive Arterial Blood Pressure and Mechanics, the Biomedical Engineering Handbook, Third Edition, Medical Devices and Systems, 2006, pp. 55-1 thru 55-16.
Finapres Medical Systems, Longterm Measurements—Double Finger Cuff System Allows a 24/7 Patient Friendly Measurement, http://www.finapres.com, Copyright Finapres 2012, 2 pages.
Forouzanfar et al., Oscillometric Blood Pressure Estimation: Past, Present, and Future, IEEE Reviews in Biomedical Engineering, 2015, 8:44-63.
Gao et al., A Simple Adaptive Transfer Function for Deriving the Central Blood Pressure Waveform From a Radial Blood Pressure Waveform, Scientific Reports, 2016, 6:33230, pp. 1-9.
Geddes et al., Characterization of the Oscillometric Method for Measuring Indirect Blood Pressure, Annals of Biomedical Engineering, 1982, 10(6):271-280.
Gizdulich et al., Models of Brachial to Finger Pulse Wave Distortion and Pressure Decrement, Cardiovascular Research, 1997, 33(3):698-705.
Hansen et al., Oscillometric Blood Pressure Measurement Used for Calibration of the Arterial Tonometry Method Contributes Significantly to Error, European Journal of Anaesthesiology, 2006, 23(9):781-787.
Ibrahim et al., Hypertension in Developing Countries, the Lancet, 2012, 380(9841):611-619.
Imholz et al., Fifteen Years Experience with Finger Arterial Pressure Monitoring: Assessment of the Technology, Cardiovascular Research, 1998, 38(3):605-616.
Jonathan et al., Investigating a Smartphone Imaging Unit for Photoplethysmography, Physiological Measurement, 2010, 31:N79-N83.
Lemay et al., Chapter 2.3, Application of Optical Heart Rate Monitoring, in Wearable Sensors, pp. 105-129, Academic Press, 2014.
Liu et al., Error Mechanisms of the Oscillometric Fixed-Ratio Blood Pressure Measurement Method, Annals of Biomedical Engineering, 2013, 41(3):587-597.
Liu et al., Patient-Specific Oscillometric Blood Pressure Measurement, IEEE Transactions on Biomedical Engineering, 2016, 63(6):1220-1228.
Liu et al. Patient-Specific Oscillometric Blood Pressure Measurement: Validation for Accuracy and Repeatability, IEEE Journal of Translational Engineering in Health and Medicine, 2017, 5:1-10.

(56) References Cited

OTHER PUBLICATIONS

Mafi et al., Oscillometric Blood Pressure Pulse Morphology, in 2011 IEEE International Symposium on Medical Measurements and Applications, pp. 413-417.
Mukkamala et al., Towards Ubiquitous Blood Pressure Monitoring via Pulse Transit Time: Theory and Practice, IEEE Transactions on Biomedical Engineering, 2015, 62(8):1879-1901.
Mukkamala et al., Toward Ubiquitous Blood Pressure Monitoring via Pulse Transit Time: Predictions on Maximum Calibration Period and Acceptable Error Limits, IEEE Transactions on Biomedical Engineering, 2018, 65(6):1410-1420.
Natarajan et al., Central Blood Pressure Monitoring via a Standard Automatic Arm Cuff, Scientific Reports, 2017, 7:14441, pp. 1-12.
National Institute of Biomedical Imaging and Bioengineering, Researchers Deploy Smart Technologies to Detect Blood Pressure and Arrhythmiaws, https://www.nibib.nih.gov/news-events/newsroom/researchers-deploy-smart-technologies-detect-blood-pressure-and-arrhythmias, 2018, 8 pages.
Office of Device Evaluation, Non-Invasive Blood Pressure (NIBP) Monitor Guidance, 1997, https://www.fda.gov/RegulatroyInformation/-Guidances/ucm080219.htm, 4 pages.
Perloff et al., Human Blood Pressure Determination by Sphygmomanometry, Circulation, 1993, 88(5):2460-2470.
Pickering et al., Ambulatory Blood-Pressure Monitoring, New England Journal of Medicine, 2006, 354:52-58.
Picone et al., Accuracy of Cuff-Measured Blood Pressure: Systematic Reviews and Meta-Analyses, Journal of the American College of Cardiology, 2017, 70(5):572-586.
Pressman et al., A Transducer for the Continuous External Measurement of Arterial Blood Pressure, IEEE Transactions on Biomedical Electronics, 1963, 10(2):73-81.
Psaty et al., Health Outcomes Associated with Antihypertensive Therapies Used as First-Line Agents: A Systematic Review and Meta-Analysis, JAMA, 1997, 277(9):739-745.
Reisinger, Here's How Many iPhones are Currently Being Used Worldwide, Fortune, 2017, http://fortune.com/2017/03/06,apple-iphone-use-worldwide/, 2 pages.
Reisinger, Apple's iPhone X Sales Have Been Strong—But Not Record-Breaking, Analyst Says, Fortune, 2018, http://fortune.com/2018/01/23/apple-iphone-x-sales-2/, 1 page.
Seo et al., Noninvasive Arterial Blood Pressure Waveform Monitoring Using Two-Element Ultrasound System, IEEE Transactions on Ultrasonics, Ferroelectrics, and Frequency Control, 2015, 62(4):776-784.
Serina et al., A Structural Model of the Forced Compression of the Fingertip Pulp, Journal of Biomechanics, 1998, 31(7):639-646.
Su, 2019 iPhone X to Have Virtual Fingerprint Reader, Smaller Notch: Report, Forbes, 2018, https://www.forbes.com/sites/jeanbaptiste/2018/02/06/2019-iphone-x-to-have-virtual-fingerprint-reader-smaller-notch-report/#7cb44ee64f76, 2 pages.
Van Montfrans, Oscillometric Blood Pressure Measurement: Progress and Problems, Blood Pressure Monitoring, 2001, 6(6):287-290.
Vappou et al., Non-Invasive Measurement of Local Pulse Pressure by Pulse Wave-Based Ultrasound Manometry (PWUM), Physiological Measurement, 2011, 32(10):1653-1662.
Wang et al., Algorithmic Principles of Remote PPG, IEEE Transactions on Biomedical Engineering, 2016, 64(7):1479-1491.
Watanabe et al., Development and Validation of a Novel Cuff-Less Blood Pressure Monitoring Device, JACC: Basic to Translational Science, 2017, 2(6):631-642.
Wesseling et al., Effects of Peripheral Vasoconstriction on the Measurement of Blood Pressure in a Finger, Cardiovascular Research, 1985, 19(3):139-145.
Wesseling, Physiocal, Calibrating Finger Vascular Physiology for Finapres, Homeostasis, 1995, 36(2-3):67-82.
Wu, Statistical Analysis of Widths and Heights of Fingerprint Images in Terms of Ages from Segmentation Data, Oct. 15, 2008, nist.gov, 5 pages.

\* cited by examiner

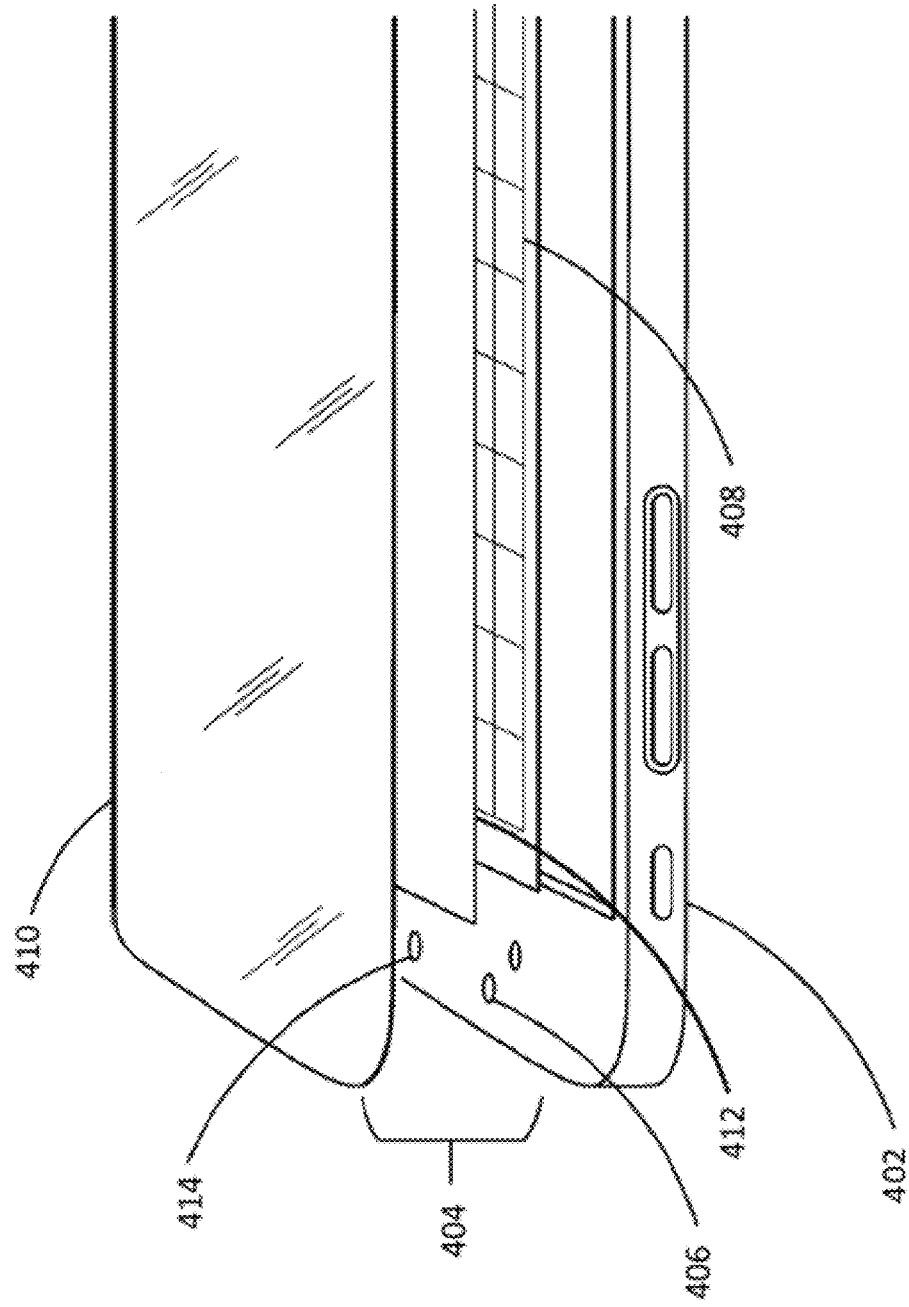

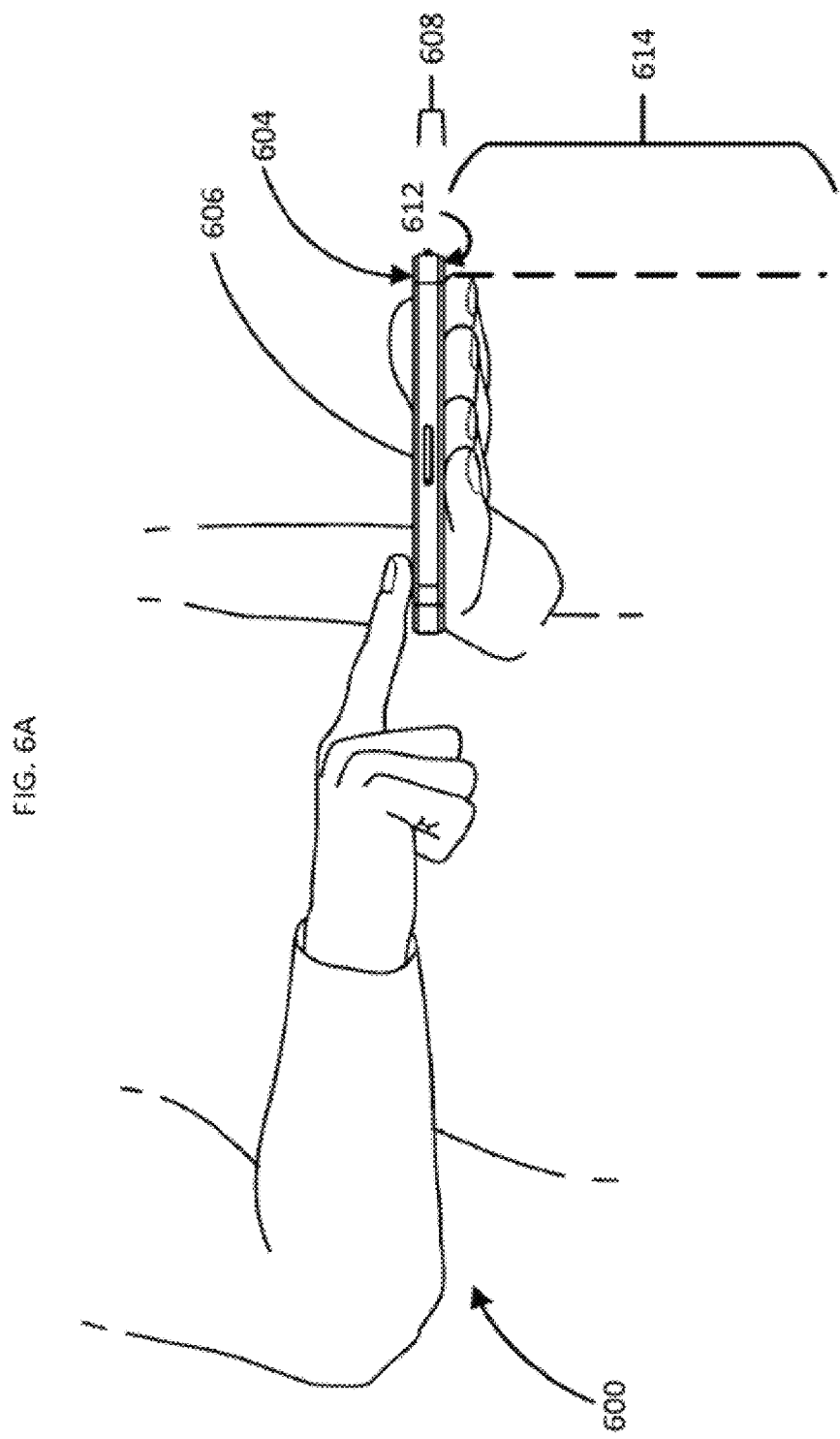

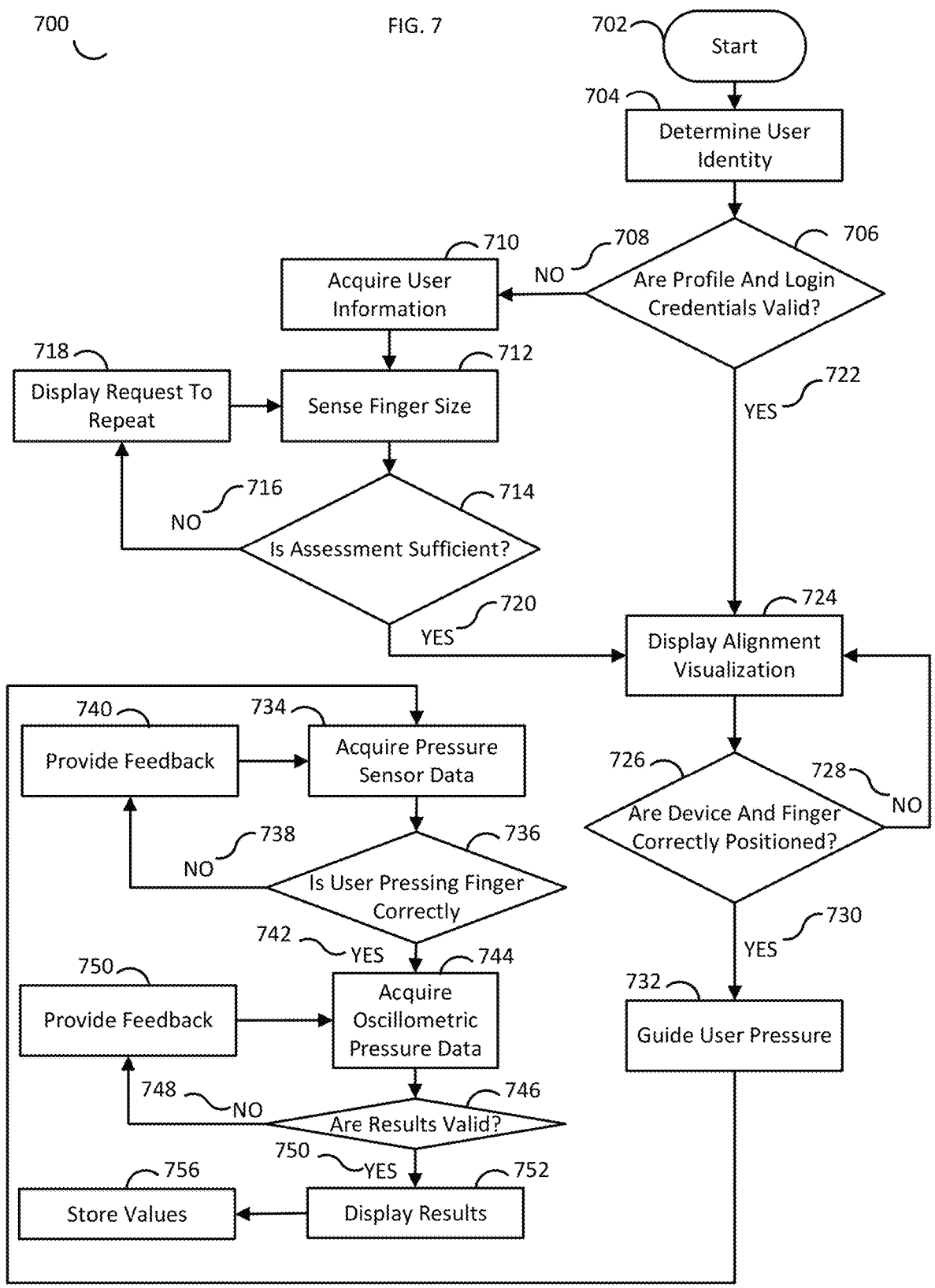

MOBILE DEVICE APPLICATIONS TO MEASURE BLOOD PRESSURE

CROSS-REFERENCE TO RELATED APPLICATIONS

This application is a national stage filing under 35 U.S.C. § 371 of International Application No. PCT/US2019/039997, filed Jun. 28, 2019, which claims priority to U.S. Provisional Application No. 62/691,472 filed Jun. 28, 2018, and U.S. Provisional Application No. 62/724,461 filed Aug. 29, 2018, both of which are incorporated herein by reference in their entirety for all purposes.

STATEMENT REGARDING FEDERALLY SPONSORED RESEARCH OR DEVELOPMENT

This invention was made with government support under EB018818 awarded by the National Institutes of Health. The government has certain rights in the invention.

BACKGROUND

Hypertension afflicts about one-fourth of the world's adult population. It is a major risk factor for stroke and heart disease and is therefore a "silent killer". Hypertension can be treated with lifestyle changes and medication, but only if it has been detected. Medical therapy is associated with a 35-40% reduction in the risk of stroke and a 15-25% reduction in the risk of heart disease. Hence, hypertension identification, monitoring, and management is an archetypical example of preventive, proactive healthcare. However, the detection of high blood pressure (BP) is often missed. An estimated 20% of people with hypertension in the US do not know they have it. Further, BP in known hypertensive patients is often uncontrolled. An estimated 53% of hypertensive patients in the US do not have their BP under control. Hypertension detection and control rates are much worse elsewhere, especially in low resource settings wherein personnel trained in BP measurement and the means for people to have their BP measured are lacking. Hypertension management is complicated by the well-known masked and white coat effects in the clinic and large BP variability amongst few measurements. In fact, ambulatory BP monitoring is now considered the gold standard for the diagnosis of high BP. Ubiquitous BP monitoring technology could improve hypertension detection by providing serial, out-of-clinic measurements in the mass population and could enhance hypertension control by providing continual feedback to the individual patient.

Several basic principles underlie the methods available for measuring BP. However, none of these methods offers ubiquitous BP monitoring capabilities, and all of them require specialized training, specialized equipment, or otherwise involve costs or processes that make them difficult to use for regular BP measurements by most of the population.

Catheterization is the gold standard method. This method measures a BP waveform by placing a strain gauge in fluid contact with blood. However, this method is invasive.

Auscultation is the standard clinical method. This method measures systolic BP (SP) and diastolic BP (DP) by occluding an artery with an inflatable cuff and detecting the Korotkoff sounds using a stethoscope and manometer during cuff deflation. The first sound indicates the initiation of turbulent flow and SP, while the fifth sound is silent and indicates the renewal of laminar flow and DP. The method is non-invasive but requires a skilled operator. Further, due to safety and ecological concerns, mercury manometers are being replaced with high maintenance aneroid manometers.

Oscillometry is the most popular non-invasive and automatic method. This method measures mean BP (MP), SP, and DP using the same inflatable cuff but with a sensor to record the pressure inside it. The recorded cuff pressure not only rises and falls with cuff inflation and deflation but also shows tiny oscillations indicating the pulsatile blood volume in the artery. The amplitude of these oscillations varies with the cuff pressure, as the arterial blood volume-transmural pressure relationship is nonlinear. Transmural pressure of an artery is defined as the internal pressure (i.e., BP) minus the external pressure (cuff pressure in this case). The BP values are estimated from the oscillogram (i.e., the oscillation amplitudes versus the cuff pressure) using an algorithm (e.g., fixed-ratios). However, automatic cuffs do not afford ubiquitous BP monitoring capabilities. That is, people in low resource settings may not have any access to such devices; others must go out of their way (e.g., to a pharmacy) to use these devices; and even people who own a device cannot carry and use them outside their homes.

Volume clamping is a non-invasive and automatic method used in research. This method measures a finger BP waveform by using a cuff with a photoplethysmography (PPG) sensor built-in to measure the blood volume. The blood volume at zero transmural pressure is estimated by slowly varying the cuff pressure. The cuff pressure is then continually varied to maintain this blood volume throughout the cardiac cycle via a fast servo-control system. The applied cuff pressure may thus equal BP. However, in addition to requiring a cuff, the method is prohibitively expensive.

Tonometry is another research method. This method measures a BP waveform by pressing a manometer-tipped probe on an artery. The probe must flatten or applanate the artery so that its wall tension is perpendicular to the probe. However, manual and automatic applanation have proven difficult. As a result, while the method should not require any calibration, the measured waveform has been routinely calibrated with a cuff in practice. Furthermore, the method is likewise costly.

The principle of pulse transit time (PTT) underlies other BP measurement attempts. PTT is the time delay for the pressure wave to travel between two arterial sites. An increase in BP causes the arteries to stiffen which, in turn, causes PTT to decline. So, PTT is often inversely correlated with BP in individual subjects. Further, PTT may be simply determined from the relative timing between proximal and distal arterial waveforms. Hence, PTT carries the advantage of possibly offering passive BP monitoring without using a cuff. However, this approach also has major disadvantages. Firstly, PTT not only changes with BP but also smooth muscle contraction (especially when measured in small arteries) and aging and disease (especially when measured in large arteries). Smooth muscle contraction occurs acutely and thus severely limits the accuracy of the approach, whereas aging and disease are longer processes that prevent PTT from being able to track chronic changes in BP such as the common development of isolated systolic hypertension due to large artery stiffening with aging. Secondly, the required calibration of PTT in units of msec to BP in units of mmHg must either be population-based and thus error-prone or involve periodic use of a BP cuff and thus not truly cuff-less.

In sum, hypertension is a major cardiovascular risk factor that is treatable, yet high BP detection, monitoring, and control rates are unacceptably low. Likewise, the ability to monitor BP during specific activities and at various times of day, in an easy on-the-go manner, is not currently possible. Ubiquitous BP monitoring technology could improve hypertension management, but oscillometric and other available non-invasive BP measurement devices employ an inflatable cuff and therefore do not afford such monitoring capabilities. While the PTT approach could potentially permit cuff-less and passive BP monitoring, its accuracy will be limited due to confounding physiology and the need for calibration. Hence, there is a need in the art for a ubiquitous, simple, method for reliable, cuff-less measurement of BP that is accessible, is something patients will readily adopt, and does not require specialized equipment.

This section provided background information related to the present disclosure, which is not necessarily prior art.

SUMMARY

In one aspect, a device including a force sensitive display screen, a photoplethysmography sensor disposed outside of and adjacent to the display screen, a processor, a memory connected to the processor containing a set of instructions is provided by the present disclosure. The set of instructions, when executed by the processor, cause the processor to display, via the display screen, a guidance visualization directing placement of a finger on the screen in a position such that at least a portion of the finger is over the display screen and a portion of the finger is over the photoplethysmography sensor, obtain varying amplitude finger blood volume oscillation data from the photoplethysmography sensor, obtain data indicating varying pressure applied by the user's finger against the display screen, and calculate a blood pressure measurement from the blood volume oscillation data and the pressure data.

The device may further include a pressure sensor integrated with the display screen such that the display screen is a pressure-sensitive display screen, and such that the pressure data is acquired from the portion of the finger over the display screen and not the portion of the finger over the photoplethysmography sensor. The pressure sensor may be a strain gauge array disposed under and substantially coextensive with an outer surface of the display screen, and the pressure data may be determined by the processor from the output of the strain gauge array. The device may be a handheld consumer mobile device.

In the device, the instructions may further cause the processor to determine a size of that portion of the finger positioned over the display screen. In the device, the instructions may further cause the processor to display, via the display screen, a prompt for a finger to be placed on the screen for measurement, and obtain data from a sensor integrated with the display screen, data indicative of the area occupied by that portion of the finger to be positioned over the display screen. In the device, the photoplethysmography sensor may be a front optical camera of the device. The front optical camera may be disposed on a surface of the device in-plane with the display screen, and the instructions may further cause the processor to obtain data indicative of total finger area and finger profile from a capacitive touch sensor of the display screen by prompting a user to outline the finger when pressed on the display screen, determine location of a crease under a distal knuckle of the finger, relative to the finger profile, determine, relative to a tip of the finger, approximately where an artery of interest is located within the finger, and determine a size and location of the guidance visualization such that when the finger is placed on the display screen, the guidance visualization prompts the user to place a tip of the finger on the display screen so that the artery of interest will be disposed over the optical camera. The device may further include a light source usable as a flash in association with taking photos via the optical camera, and also usable as a dedicated photoplethysmography sensor light source. 0. In the device, red-green-blue channels of the optical camera can be used to derive blood volume oscillations of the finger.

In the device, the guidance visualization can be determined using measurements of the user's finger dimensions. In the device, the display screen may further include an integrated fingerprint scanner, and the instructions may further cause the processor to obtain the measurements of the finger using the fingerprint scanner of the display screen.

In the device, the guidance visualization may depict a visual guide of a size and location that, when a finger is pressed in accordance with the visualization, a digital artery along a side of the finger will be disposed over the photoplethysmography sensor.

In another aspect, a method for obtaining a blood pressure measurement is provided by the present disclosure. The method includes prompting a user to hold a mobile device at heart level, prompting a user to press one of the user's fingers against a location on a display screen of the mobile device, acquiring force data indicative of force applied by the user's finger against the display screen, measuring blood volume oscillations within at least one artery of the user's finger via a sensor of the mobile device while the user is pressing the finger on the display screen, calculating a blood pressure reading based upon the force data and the measured blood volume oscillations; and displaying the blood pressure reading to the user via the display screen of the mobile device.

The method may further include the step of performing a user initialization including obtaining a measurement of dimensions of a portion of the user's finger. In the method, the measurement of dimensions of a portion of the user's finger may be determined by obtaining a cuff-based blood pressure measurement, and a total force measurement of force applied by the portion of the user's finger against the display screen, and calculating area of the portion of the user's finger based upon the two measurements.

The method may further include determining a distance from a tip of the user's finger to an approximate location of the at least one artery based upon general anatomical data of human fingers, retrieving data indicative of a distance from an optical sensor of the mobile device to a proximate edge of the display screen, and the step of prompting the user to press one of the user's fingers against the display screen may include prompting the user to press a portion of the user's finger on the display screen such that the approximate location of the artery of interest will be disposed over the optical sensor.

In the method, a measurement of dimensions of a portion of the user's finger pressed against the display screen may be acquired while the force data is being acquired.

The method may further include using output of device sensors to correct a blood pressure reading for deviations due to the user not holding the device at heart level.

The method may further include the step of, after the user has pressed the finger against the display screen, determining whether the finger has been placed at the identified location on the display screen, and if not, displaying a prompt to the user indicating how the user should adjust finger location.

In the method, the step of prompting the user to press one of the user's fingers against a location of the display screen of the mobile device may include displaying an outline of a portion of a finger on the display screen at the location. In the method, dimensions of the outline of the portion of the finger may be determined based upon a measured size of the user's finger.

The method may further include obtaining a measurement of area of the portion of the user's finger pressed against the screen, obtaining the data indicative of force applied against the display screen from a sensor array disposed beneath a surface of the display screen, and calculating pressure data from the area measurement and the force data.

In yet another aspect, a system including a pressure-sensitive user display screen, an optical sensor disposed outside of the display screen, aa processor, and a memory connected to the processor, having instructions stored thereon is provided by the current disclosure. The instructions, when executed by the processor, cause the processor to display, via the display screen, an indication to a user of a finger pressing location on the pressure-sensitive user display screen, display a real time guidance to the user via the display screen to vary pressure of the finger against the pressure-sensitive user display screen, receive pressure data from the pressure-sensitive user display screen while the user is applying pressure, receive output data of the optical sensor, and calculate blood volume oscillations from the optical sensor output data, calculate an oscillogram from the blood volume oscillations and pressure data, and display a blood pressure measurement to a user based on the oscillogram.

In the system, displaying the real time guidance to the user may include displaying an indication of varying target pressure and a real time indication of actual applied pressure.

In the system, the instructions may further cause the processor to send the blood pressure measurement and a heart rate measurement obtained from the same optical sensor to a remote server for storage in a health record of the user.

In the system, the pressure-sensitive user display screen may include a strain gauge array from which the pressure data is generated, disposed coextensively and beneath an outer surface of the display screen and not beneath the optical sensor.

In the system, the pressure-sensitive user display may be a touch screen, and the instructions may further cause the processor to obtain a customized measurement of a user's finger by prompting the user to provide a finger profile via the touch screen display.

In the system, the instructions may further cause the processor to prompt the user to press one of the user's fingers against a location of the display screen within an outline displayed on the display screen at a location such that when the user's finger is placed within the outline, an artery of interest of the finger will be disposed over the optical sensor.

BRIEF DESCRIPTION OF THE DRAWINGS

The present invention will hereafter be described with reference to the accompanying drawings, wherein like reference numerals denote like elements.

FIG. 7 is an illustrative process flow chart describing how exemplary methods disclosed herein may operate.

DETAILED DESCRIPTION

Figure 1:
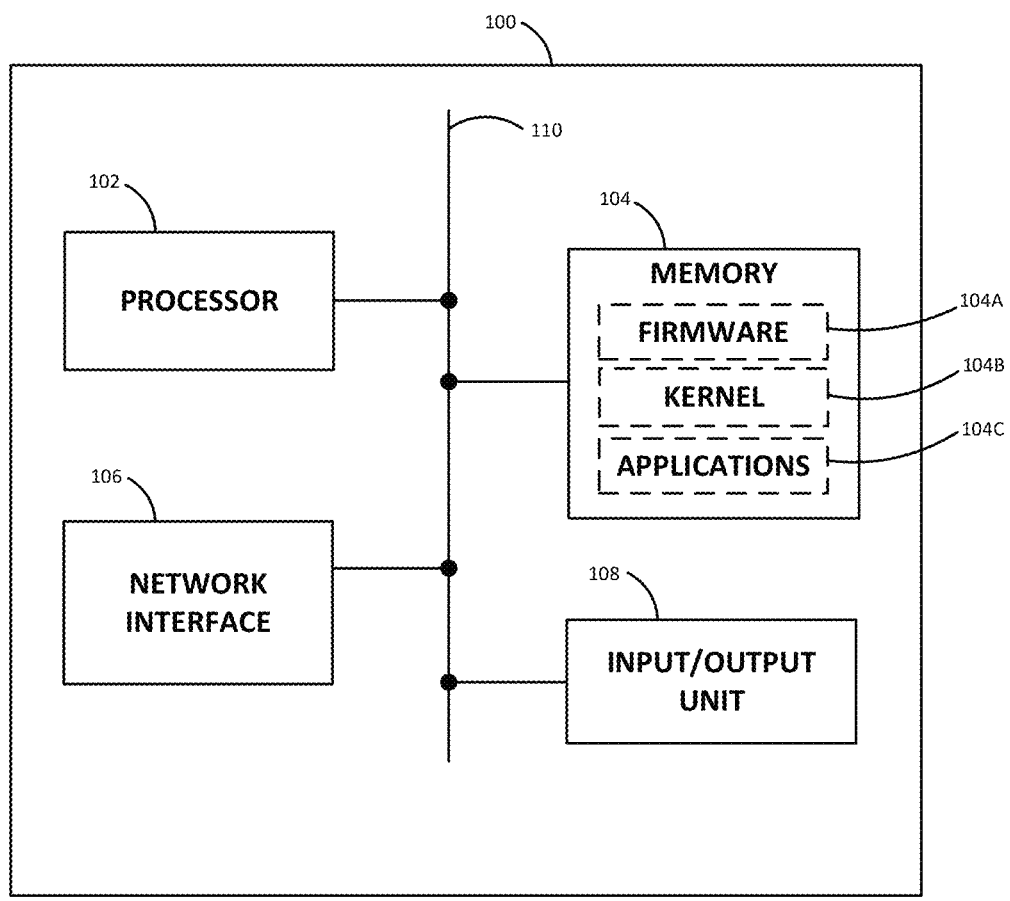
FIG. 1 is an illustrative block diagram of a computer system that may execute some or all of the method of FIG. 7, in accordance with example embodiments.

As described herein, various systems and techniques can be employed to allow for a cuffless, calibration-free blood pressure measurement from a user's finger, without the need for specialized equipment. For example, standard consumer mobile devices having pressure sensitivity already integrated within their touch screens can be programmed to determine a user's blood pressure. By leveraging the screen of a mobile device, the user can place her finger directly onto a silhouette or other mapping of the finger to ensure precise placement. The mobile device's standard optical camera can then be used as a photoplethysmography (PPG) sensor, and the pressure sensitivity of the screen can determine applied pressure. The user then presses her finger uniformly on the screen and camera to slowly change (e.g., increase) the applied finger pressure. The mobile device guides the finger actuation by visual or other feedback so that pressure can vary from a sub-diastolic to a supra-systolic level. From the pressure and PPG readings, the device can compute and output a measurement of systolic and diastolic blood pressure at the finger or even the arm. The blood pressure measurement principle of this finger pressing method is oscillometry, which is employed by most automatic cuff devices, yet this principle can be leveraged using only standard, readily-available mobile devices such as cellular smartphones.

Because the systems and methods herein allow for easy, accurate, on-the-go measurement of blood pressure, more health data can be obtained for at-risk individuals. Likewise, groups who previously had no or limited access to blood pressure measurements can readily obtain readings without having to purchase or operate specialized equipment. Additionally, companies and institutions that may benefit from greater patient data (e.g., insurers or clinics) could be provided access to the blood pressure data if the users consent.

When the programming that transforms PPG and pressure readings into blood pressure measurements takes the form of a mobile application, the software can be readily updated to give interactive guidance to users who struggle with obtaining accurate measurements. Likewise, users can undergo an initialization step to take a precise measurement of their fingers using only the screen of their mobile device. This even further increases accuracy.

The software and processing that returns a blood pressure measurement can be operated on the mobile device itself or remotely. For example, a remote server may store user's blood pressure readings taken from the mobile device and determine if the readings are valid or demonstrate cause for concern given the user's health records. Alternatively, the software and processing can be operated entirely on the device or a local computer.

Before any embodiments of the disclosed subject matter are explained in detail, it is to be understood that the disclosed subject matter is not limited in its application to the details of construction and the arrangement of components set forth in the following description or illustrated in the following drawings. The disclosed subject matter is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "in communication with," "connected to," "supported," and "coupled" and variations thereof are used broadly and encompass both direct and indirect electrical, wireless, analog, digital, local, and remote forms of communication, connections, supports, and couplings. Further, "connected" and "coupled" are not restricted to physical or mechanical connections or couplings.

The following discussion is presented to enable a person skilled in the art to make and use embodiments of the disclosed subject matter. Various modifications to the illustrated embodiments will be readily apparent to those skilled in the art, and the generic principles herein can be applied to other embodiments and applications without departing from embodiments of the disclosed subject matter. Thus, embodiments of the disclosed subject matter are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the disclosed subject matter. Skilled artisans will recognize the examples provided herein have many useful alternatives and fall within the scope of embodiments of the disclosed subject matter.

Hardware Usable for the Disclosed Systems and Methods

FIG. 1 is a simplified block diagram exemplifying a computing device 100, illustrating some of the components that could be included in a computing device arranged to operate in accordance with the embodiments herein. Computing device 100 could be a client device (e.g., a device actively operated by a user), a system or server device (e.g., a device that provides computational services to client devices), or some other type of computational platform. Some server devices may operate as client devices from time to time in order to perform particular operations, and some client devices may incorporate server features. The computing device 100 may, for example, be used to execute (e.g., via the processor 102 thereof) may be configured to execute, in whole or in part, the method of FIG. 4. In one embodiment, computing device 100 is a mobile device such as a cellular phone or tablet.

In this example, mobile device 100 includes a processor 102, memory 104, network interface 106, and one or more input/output units 108, all of which may be coupled by a system bus 110 or a similar mechanism. In some embodiments, computing device 100 may include other components and/or peripheral devices (e.g., detachable storage, scanner accessories, light sources, pressure sensors, and so on).

Processor 102 may be one or more of any type of computer processing element, such as a central processing unit (CPU), a co-processor (e.g., a mathematics, graphics, or encryption co-processor), a digital signal processor (DSP), a network processor, a mobile-specific processor, and/or a form of integrated circuit or controller that performs processor operations. In some cases, processor 102 may be one or more single-core processors. In other cases, processor 102 may be one or more multi-core processors with multiple independent processing units. Processor 102 may also include register memory for temporarily storing instructions being executed and related data, as well as cache memory for temporarily storing recently-used instructions and data.

Memory 104 may be any form of computer-usable memory, including but not limited to random access memory (RAM), read-only memory (ROM), and non-volatile memory. This may include flash memory, hard disk drives, solid state drives, re-writable compact discs (CDs), re-writable digital video discs (DVDs), and/or tape storage, as just a few examples. Computing device 100 may include fixed memory as well as one or more removable memory units, the latter including but not limited to various types of secure digital (SD) cards. Thus, memory 104 represents both main memory units, as well as long-term storage. Other types of memory may include biological memory.

Memory 104 may store program instructions and/or data on which program instructions may operate. By way of example, memory 104 may store these program instructions on a non-transitory, computer-readable medium, such that the instructions are executable by processor 102 to carry out any of the methods, processes, or operations disclosed in this specification or the accompanying drawings.

As shown in FIG. 1, memory 104 may include firmware 104A, kernel 104B, and/or applications 104C. Firmware 104A may be program code used to boot or otherwise initiate some or all of computing device 100. Kernel 104B may be an operating system, including modules for memory management, scheduling and management of processes, input/output, and communication. Kernel 104B may also include device drivers that allow the operating system to communicate with the hardware modules (e.g., memory units, networking interfaces, ports, and busses), of computing device 100. Applications 104C may be one or more user-specific software programs, such as web browsers or email clients, as well as any software libraries used by these programs. Memory 104 may also store data used by these and other programs and applications. In various embodiments disclosed herein, memory 104 may contain an application that executes techniques and computations for determining blood pressure based on various user inputs and sensor outputs. Memory 104 may also store historical blood pressure and heart rate measurements for multiple user profiles.

Network interface 106 may take the form of one or more wireline interfaces, such as Ethernet (e.g., Fast Ethernet, Gigabit Ethernet, and so on). Network interface 106 may also support communication over one or more non-Ethernet media, such as coaxial cables or power lines, or over wide-area media, such as Synchronous Optical Networking (SONET) or digital subscriber line (DSL) technologies. Network interface 106 may additionally take the form of one or more wireless interfaces, such as the various cellular networks, IEEE 802.11 (Wifi), BLUETOOTH®, global positioning system (GPS), or other wide-area wireless interface. However, other forms of physical layer interfaces and other types of standard or proprietary communication protocols may be used over network interface 106. Furthermore, network interface 106 may comprise multiple physical interfaces. For instance, some embodiments of computing device 100 may include Ethernet, BLUETOOTH®, and Wifi interfaces. In various embodiments disclosed herein, the network interface may communicate by Internet protocol or other protocols with a remote server storing health data of a user of the device 100.

Input/output unit 108 may facilitate user and peripheral device interaction with example computing device 100. I/O units 108 may include input devices like a touch (e.g., capacitive touch) and/or pressure sensitive screen, an infrared camera, electrodes, an optical camera, a microphone, and the like. Similarly, input/output unit 108 may include one or more types of output devices, such as a display screen, speaker, flash/light source, and/or one or more light emitting diodes (LEDs). Additionally or alternatively, computing device 100 may communicate with other devices using a universal serial bus (USB) or high-definition multimedia interface (HDMI) port interface, for example.

In some embodiments, one or more instances of computing device 100 may be deployed to support a clustered architecture. The exact physical location, connectivity, and configuration of these computing devices may be unknown and/or unimportant to client devices. Accordingly, the computing devices may be referred to as "cloud-based" devices that may be housed at various remote data center locations.

Figure 2:
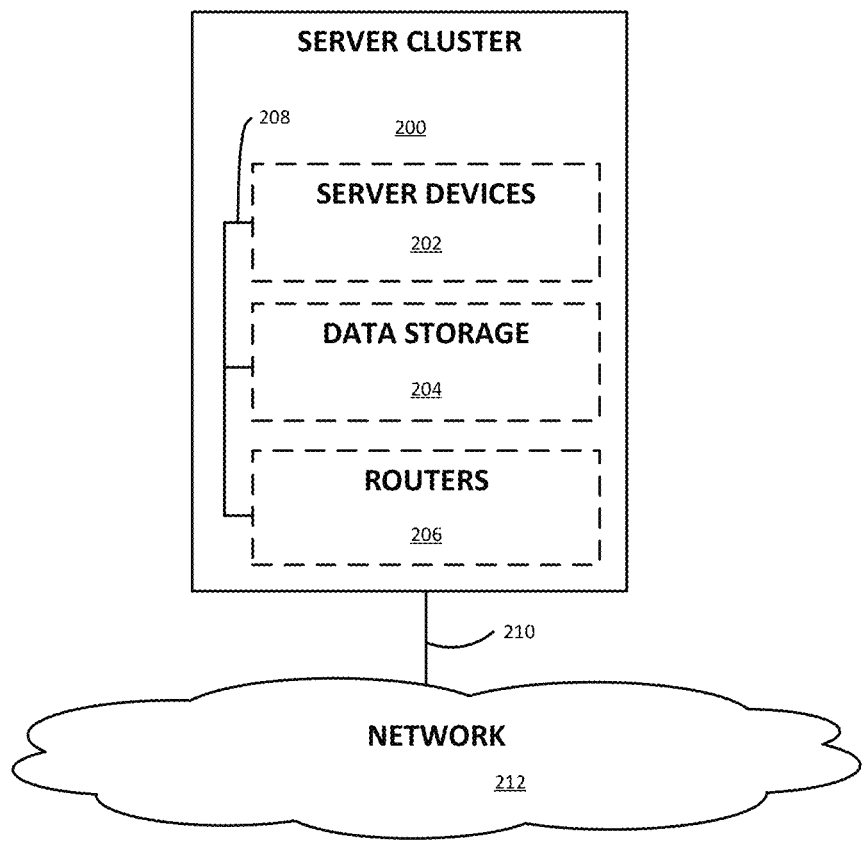
FIG. 2 is an illustrative block diagram of a server cluster that may execute some or all of the method of FIG. 7 and may interact with the system of FIG. 1, in accordance with example embodiments.

FIG. 2 depicts a cloud-based server cluster 200 in accordance with example embodiments. In FIG. 2, various computations, memory storage/retrieval, and other operations of a computing device (e.g., mobile device 100 of FIG. 1) may be distributed between server devices 202, data storage 204, and routers 206, all of which may be connected by local cluster network 208. The number of server devices 202, data storages 204, and routers 206 in server cluster 200 may depend on the computing task(s) and/or applications assigned to server cluster 200 (e.g., the execution and/or training of machine learning models and/or algorithms, the calculation of feature data such as persistent homology barcodes or MWCGs, and other applicable computing tasks/applications). The server cluster 200 may, for example, be configured to execute (e.g., via computer processors of the server devices 202 thereof), in whole or in part, the method of FIG. 4.

For example, server devices 202 can be configured to perform various computing tasks of mobile device 100. Thus, computing tasks can be distributed among one or more of server devices 202. To the extent that these computing tasks can be performed in parallel, such a distribution of tasks may reduce the total time to complete these tasks and return a result. For purpose of simplicity, both server cluster 200 and individual server devices 202 may be referred to as a "server device." This nomenclature should be understood to imply that one or more distinct server devices, data storage devices, and cluster routers may be involved in server device operations.

Data storage 204 may be data storage arrays that include drive array controllers configured to manage read and write access to groups of hard disk drives and/or solid state drives. The drive array controllers, alone or in conjunction with server devices 202, may also be configured to manage backup or redundant copies of the data stored in data storage 204 to protect against drive failures or other types of failures that prevent one or more of server devices 202 from accessing units of cluster data storage 204. Other types of memory aside from drives may be used. For example, data storage 204 may be used to store sensor output of the mobile device 100, electronic medical records of the user, and user profiles.

Routers 206 may include networking equipment configured to provide internal and external communications for server cluster 200. For example, routers 206 may include one or more packet-switching and/or routing devices (including switches and/or gateways) configured to provide (i) network communications between server devices 202 and data storage 204 via cluster network 208, and/or (ii) network communications between the server cluster 200 and other devices via communication link 210 to network 212.

Additionally, the configuration of cluster routers 206 can be based at least in part on the data communication requirements of server devices 202 and data storage 204, the latency and throughput of the local cluster network 208, the latency, throughput, and cost of communication link 210, and/or other factors that may contribute to the cost, speed, fault-tolerance, resiliency, efficiency and/or other design goals of the system architecture.

As a possible example, data storage 204 may include any form of database, such as a structured query language (SQL) database. Various types of data structures may store the information in such a database, including but not limited to tables, arrays, lists, trees, and tuples. Furthermore, any databases in data storage 204 may be monolithic or distributed across multiple physical devices.

Server devices 202 may be configured to transmit data to and receive data from cluster data storage 204. This transmission and retrieval may take the form of SQL queries or other types of database queries, and the output of such queries, respectively. Additional text, images, video, and/or audio may be included as well. Furthermore, server devices 202 may organize the received data into web page representations. Such a representation may take the form of a markup language, such as the hypertext markup language (HTML), the extensible markup language (XML), or some other standardized or proprietary format. Moreover, server devices 202 may have the capability of executing various types of computerized scripting languages, such as but not limited to Python, PHP Hypertext Preprocessor (PHP), Active Server Pages (ASP), JavaScript, and/or other languages such as C++, C#, or Java. Computer program code written in these languages may facilitate the providing of web pages to client devices, as well as client device interaction with the web pages.

Oscillometric Principles

Next, a brief overview of certain physiological principles underpinning oscillometry and blood pressure measurements will be provided as background for a better understanding of why the various techniques and methods herein are able to operate with the equipment described above. Oscillometry is the basic principle underlying many current, non-invasive devices for measuring blood pressure. In the most common implementation, the method measures mean blood pressure (MP), systolic blood pressure (SP), and diastolic blood pressure (DP) using an inflatable cuff with a sensor to record the pressure inside it. The cuff is placed over a large artery in a patient's upper arm, for example the brachial artery. The cuff is inflated to impose significant pressure on the artery to a supra-systolic level and then slowly deflated to a sub-diastolic level, and the sensor inside the cuff records pressure during the measurement process. The recorded cuff pressure not only rises and falls with cuff inflation and deflation but also shows tiny oscillations indicating the pulsatile blood volume in the artery. The amplitude of these oscillations varies with the cuff pressure, as the arterial blood volume-transmural pressure relationship is nonlinear. Thus, the sensor also records these variable-amplitude blood volume oscillations as well. Transmural pressure of an artery is defined as the internal pressure (i.e., BP) minus the external pressure (cuff pressure in this case). The BP values are estimated from the oscillogram (i.e., the oscillation amplitudes versus the cuff pressure) using an algorithm. One algorithm is to estimate mean BP as the cuff pressure at which the oscillogram is maximal and systolic and diastolic BP as the cuff pressures at which the oscillogram are some fixed ratios of its maximal value (i.e., the "fixed ratio" method). Another algorithm is to estimate diastolic BP and systolic BP as the cuff pressures at which the oscillogram has maximal and minimal slopes, respectively (i.e., the "derivative" method). A third algorithm is to estimate the BP values based on a physics-based model (i.e., "patient-specific" method).

One advantage of cuff-based oscillometric blood pressure measuring techniques is that, given the large size of most cuffs, the comparatively large volume of the brachial artery in the upper arm, and the controlled amount of pressure that can be applied, precise positioning of the cuff and sensor is generally not required. In other words, an advantage of standard oscillometry methods is that the cuff need not be positioned carefully (in comparison to auscultation, for example). In fact, the pressure sensor is not even located in the cuff. Rather, it is in the device and connected to the cuff via an air-filled tube. However, along with the size and pressure advantages of cuff-based systems come many disadvantages. One significant and primary disadvantage is that such methods do not afford ubiquitous BP monitoring capabilities. In other words, they are limited by the need to have large, specialized cuffs, with integrated sensors and a connection to equipment needed to inflate the cuff to produce the cuff pressure. Thus, people in low resource settings may not have any access to such devices; others must go out of their way (e.g., to a pharmacy) to use these devices; and even people who own a device cannot carry and use them outside their homes. Similarly, individuals with low or compromised mobility may not conveniently be able to move to a location having a cuff-based systems on their own or use the cuff-based system on their own.

In contrast, in systems and methods disclosed herein, blood pressure can be easily and accurately measured using the oscillometric principle, but with much smaller and more readily-available equipment. In some embodiments, the systems and methods herein can be implemented via standard consumer mobile phones and mobile devices without the need for any specialized hardware or modifications. For example, blood pressure can be measured from a user's finger including the fingertip at the transverse palmar arch artery. In other embodiments, blood pressure can be measured from the digital arteries extending along the sides of each of the user's fingers. The PPG or oscillation data can be acquired from a standard camera of a mobile device, and pressure data can be acquired directly from a screen. Moreover, by using native pressure arrays within a screen, pressure measurements can be adaptable to the size and profile of a finger, and can allow for measurements to be taken from multiple arterial branches at a user's preference.

Figure 3:
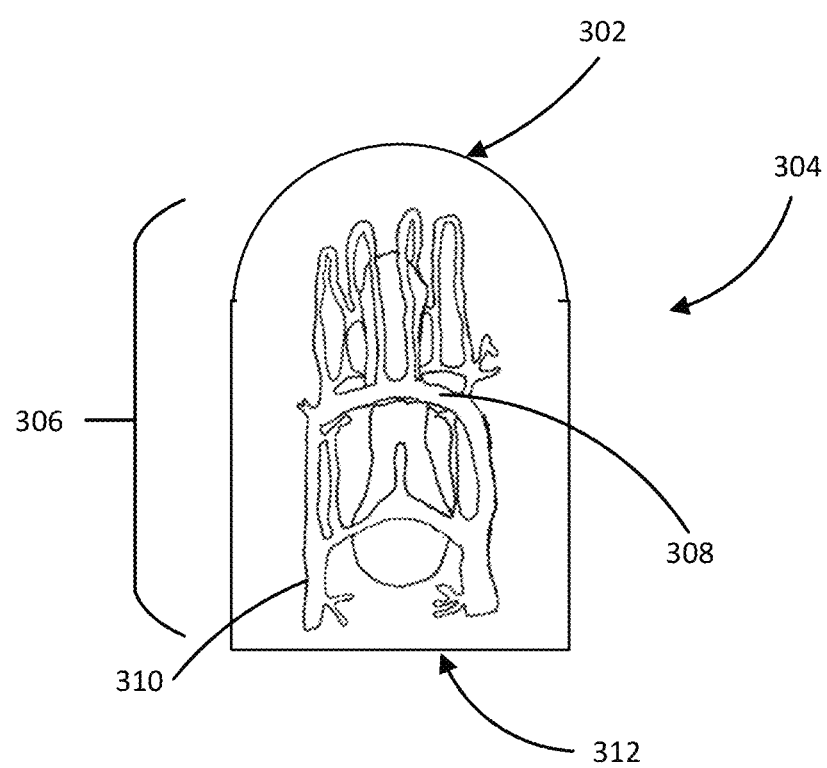
FIG. 3 is an illustrative diagram of the general placement and orientation of arteries in a human finger.

FIG. 3 shows a general depiction of the placement and orientation of the arterial network 306 of a human index finger 302. The depiction shows the underside or "fingerprint" side 304 of the finger 302; the upper or "fingernail" side of the finger 302 would be opposite the depicted fingerprint side 304. The underside crease of the last or distal knuckle 312 of the finger is shown below the fingertip 302. The radialis indicis artery 310 (the radial artery of index finger) is a branch of the radial artery that provides blood to the index finger. As it approaches the end of the fingertip 302, it branches across the finger forming the transverse palmar arch artery 308. This artery 308 of the finger is more easily accessible and thus the inventors have found it to be a convenient place for taking fingertip-based blood pressure measurements. Likewise, the inventors have discovered that users are able to align their transverse artery 308 on a sensor in accordance with the methods disclosed herein. As noted above, the digital/radial arteries 310 along the sides of a finger could also be used. In fact, because of the advantages of the systems and techniques disclosed herein, some embodiments could allow a user to choose whether to measure blood pressure from any branch of the arterial network 306, such as the digital arteries 310 on either side of the finger or the transverse palmar arch artery 308. Similarly, if a device is unable to obtain a reliable or valid blood pressure measurement from one artery location the device could be programmed to automatically prompt the user to reposition her finger, turn or roll her finger, or reorient her finger so that a PPG sensor can address a different arterial location. The artery from which the most reliable readings are obtained could be stored in a user profile.

Devices and Screen Prompts Usable for the Disclosed Systems and Methods

FIG. 4 is a set of perspective diagrams showing various devices that may be used to implement the methods and techniques disclosed herein. FIG. 4(a) is a partially-exploded diagram of mobile device 402, such as a standard, off the shelf, consumer cellular smartphone. However, it should be understood that the various components referenced below and used in the techniques described herein could also be present in tablets or other mobile devices, or customized equipment could be made having such components. The device 402 includes a display screen 412, which may be a typical high resolution LED/LCD mobile device screen, such as a Retina screen. As is typical of many mobile phone devices, a "notch" or other similar area 404 exists at one end of the device 402, on the outer front surface, or "top," display side 410 of the device. The notch area 404 may contain a front-facing optical sensor 406, and may optionally contain an infrared sensor 414 in addition to or instead of the front facing sensor 406. The display area 412 comprises a strain gauge array 408 disposed beneath the outer glass surface 410 of the screen area 412. The strain gauge array 408 is shown as existing coextensively with the screen area 412 and coextensive with the glass cover 410, but notable is not beneath the notch area 404. The strain gauge array is in a parallel plane with the outer surface 410 and is integrated into or forms a part of the display screen 412.

In one embodiment, the front facing sensor 406 is a standard optical camera customary to many modern mobile phone devices, but can be employed as a PPG sensor for purposes of measuring blood pressure. It presents a small profile in comparison to the total size of the display screen area 412. The output of the camera 406 may include standard "RGB" channels, which can be preferentially leveraged to better isolate data indicative of blood volume oscillations (including heart beats and heart rate). The light source for image data acquisition by the camera 406 may be ambient light, the light emanating from the screen area 412, and/or a dedicated light source such as a camera flash. Alternatively, a dedicated infrared sensor 414 may be configured to acquire image data from specific red/infrared wavelengths suitable for detecting arterial blood flow, which may provide a superior PPG sensor as compared to other camera types. In another embodiment, sensor 406 is a camera that outputs red, green, and blue (RGB) channel information, and can be used as reflectance-mode PPG sensor array. The RGB camera can operate as multiple photodetectors and a camera flash integrated on the front of device 402 could operate as a light source providing specific wavelengths of light that make blood volume readings more accurate and obtainable. Each pixel in a RGB video output can thus provide blood volume waveforms at the three wavelengths. That is, the RGB video can construct a "PPG image". From the PPG image, "hot spots" in the finger can be identified to measure the blood volume from a target artery of interest. The RBG camera, already built in the mobile device, may be leveraged to measure the blood volume oscillations The strain gauge array 408 detects pressure applied to the surface 410 of the screen 412. In one embodiment, the strain gauge array 408 may be an array implementing a screen pressure system such as Apple's "3DTouch" or certain Huawei and Xiaomi model phones. The screen pressure system may also allow accurate measurements of finger contact area. Certain phones may have differing camera and/or PPG sensor and screen arrangements. In one embodiment, the strain gauge array 408 is, in essence, a force sensor that outputs a voltage signal in proportion to detected inward/downward force applied on any location of the exterior glass 410 of the screen. For example, output voltage could take on a set number of values (e.g., 400 values) ranging from 0 to 0.83 (or some other range of voltage values) and a simple equation could be obtained by placement of high density weights and used to compute force from such voltage (e.g., F=443.75V, where F is represented by grams and V is volts). Finger pressure may be computed as the outputted force divided by the finger contact area for the portion of a finger the user presses against the screen. In devices that provide localized force output specific to points on the surface 410 of the screen area 412, finger area can be measured simultaneously with force. A user may press her fingertip uniformly on the front camera and screen, the variable-amplitude blood volume oscillations and applied finger pressure may be measured by the camera and strain gauge array 408, and BP can then be computed based on the measured oscillations. BP can be calculated based on the oscillations and/or a generated oscillogram using the standard fixed-ratio algorithm, the standard derivative algorithm, a patient-specific algorithm, or another algorithm. These algorithms may also be combined in various manners to estimate BP.

BP can also be estimated by generating an oscillogram based on the oscillations, computing finger pressure via one of the algorithms, and then computing arm pressure via a transfer function or regression algorithm. BP can be estimated using empirical methods or physics based methods. The strain gauge array 408 may also indicate the location of force being applied; this feature may be adapted to help guide positioning of a fingertip on the screen for purposes of ensuring proper placement during blood pressure measurements. Alternatively, or in addition, the capacitive or "touch" screen functionality of a mobile device's screen could also be used to obtain a measurement of the size and profile of a finger. For example, as a user presses and releases her finger on a screen, the capacitive readings can be monitored to determine the evolving finger pressing contact area. In some mobile devices, the screens have embedded fingerprint sensors which could also be leveraged to determine finger pressing contact area at maximum pressure or at multiple pressures. The force from the strain gauge array 408 divided by the finger pressing contact area gives the applied finger pressure.

Figure 4B:
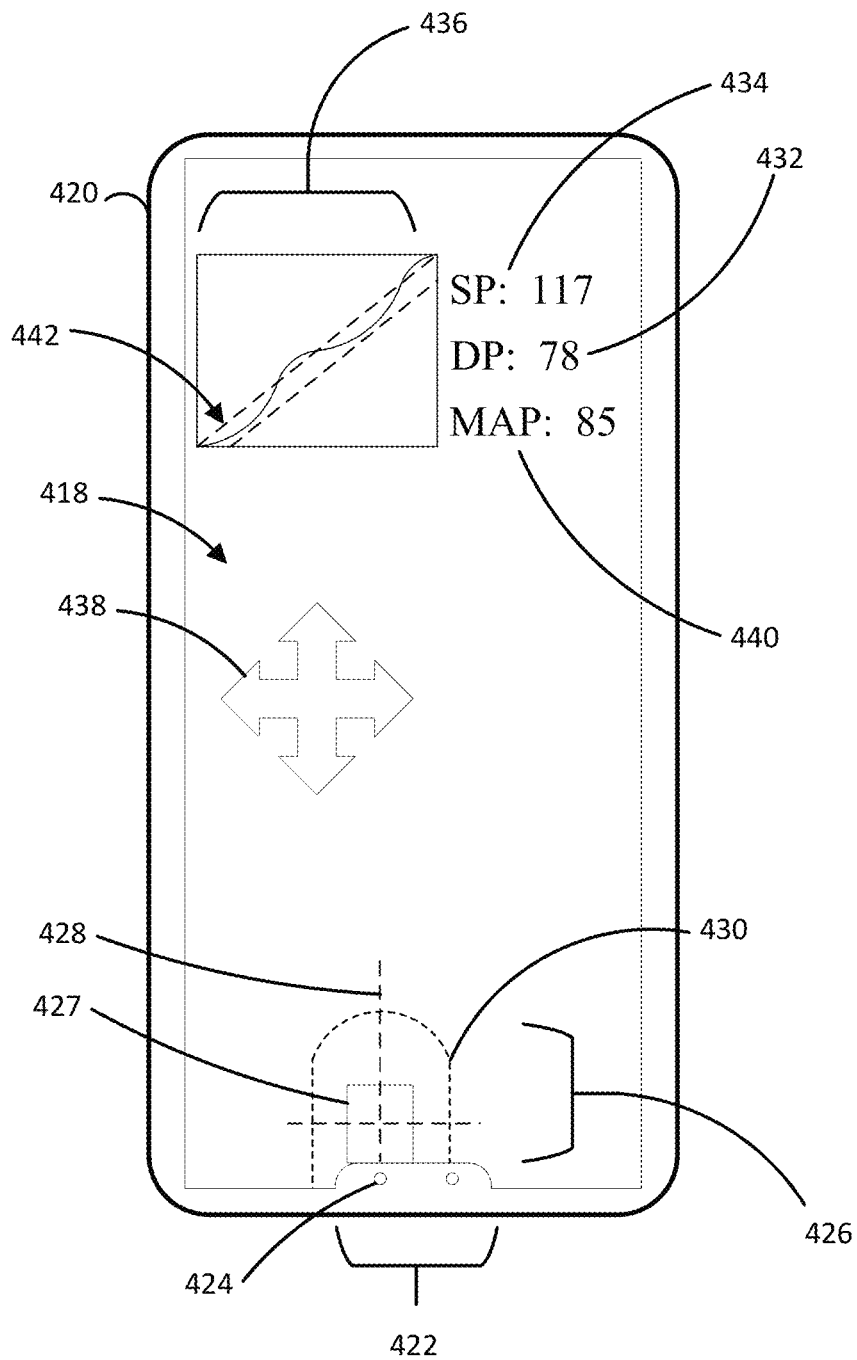
FIG. 4 is a set of illustrative block diagrams showing one example user device that could be used in association with the methods and example embodiments disclosed herein.

FIG. 4(b) depicts a typical consumer mobile device 420, with the screen 418 turned 'on' and an application in accordance with certain embodiments herein running on the device 420. As can be seen, the device 420 is oriented upside-down in comparison to how the device would customarily be held by a user. In other words, the notch area 422 is located at the bottom of the screen (if held vertical) or at the proximate end toward the user (if held horizontal). Thus, the camera sensor 424 is nearest the user. In one embodiment (to be further described below), the internal memory of device 420 stores a set of software instructions which, when executed by the on board processor implement an executable program (or, colloquially, an 'app'). The program may display on screen 418 a targeting visualization 426. The targeting visualization 426 is located on screen 418 near the camera 424 and notch 422, and helps a user position her finger properly for blood pressure measurement. The targeting visualization 426 may take a variety of forms, which may include a set of cross-hairs and/or a finger silhouette or oval shape or a rectangular box 427. The program may also cause the processor of the device 420 to display on screen 418 an indication of systolic pressure (SP) 434, an indication of diastolic pressure 432, and/or an indication of mean arterial pressure (MAP) 440. Standard brachial (arm) BP, which is the proven cardiovascular risk factor, may also be derived. While finger and brachial MP and DP are similar, finger SP is higher than brachial SP due to arterial wave reflection. Brachial SP may be estimated by simple transformations of finger BP. For example, since the ratio of finger SP to brachial SP may decrease with age, an age-dependent scaling of finger SP could be applied to estimate brachial SP. Alternatively, a transfer function may be applied to more accurately estimate brachial BP from finger BP. The transfer function would require input of the finger BP waveform, which could be obtained with the patient-specific algorithm. Another possibility is to estimate brachial SP from finger DP and MP using empirical formulas designed for brachial BP (e.g., MP=(1/3)*SP+(2/3)*DP).

The screen 418 may also display an indication of the real time pressure data 436 from the strain gauge array of the device 420. In this way, a user can see in real time whether she is applying enough, too much, or not enough force when pressing her finger against screen 418. A target band of pressure 442 could be overlaid onto the pressure data 436 to provide a user a visual indication of when too much or too little pressure is being applied. As depicted, the plotted line of the real time pressure indicator 436 shows force over time. As the user presses harder, the line moves up, and likewise as the user presses less, the line advances downward. The 'app' could be programmed to provide visual or auditory alerts to the user to ensure her pressure stays within the guidebands 442, so that pressure on the target artery advances from sub-diastolic to supra-systolic.

Additionally, screen 418 could also display to the user a visual indication 438 of needed directional shifting, turning, or moving, to ensure the finger is being pressed against the screen in a proper way. This is a helpful feature for ensuring that the transverse palmar arch artery of a user's fingertip winds up placed where it should be (i.e., near the PPG sensor) for proper blood pressure measurement. For example, if the strain gauge array, capacitive touch screen sensors, and/or camera (alone or in combination) detect that not enough of a user's finger is placed over the screen area 418, a visual "up" arrow 438 could be displayed along with a silhouette 430 showing where the finger should be moved. Alternatively, if the appropriate amount of the user's finger is placed over the screen area 418, but the finger is rotated toward the side, a visual indication arrow or demonstration animation can be presented to the user on the screen area 418 to explain to the user which way to rotate the fingertip to ensure the correct side of the finger is being pressed. Notably, these animations are presented on the same screen 418 on which the user is pressing.

In other embodiments, if the programming of the device 420 determines that valid blood pressure measurements are not being obtained, despite several attempts, the screen 418 could automatically prompt the user (by animations, guidance visualizations, text, or audio) to attempt a different finger orientation so as to address a different arterial branch against the camera 424. For example, if a user first presses her fingerprint area over silhouette 430 multiple times without valid results, the screen could prompt the user to apply the side of her finger by showing an animation and altering the size and shape of silhouette 430 accordingly. Then, the device would make multiple attempts to obtain a valid blood pressure reading from, e.g., the digital artery on one side of a finger. If that also proved unsuccessful, the digital artery on the other side of the finger could be attempted, or a different finger or thumb could be attempted. Because the pressure sensing of the screen is coextensive with the display screen, it is adaptable to multiple different finger orientations.

Figure 4C:
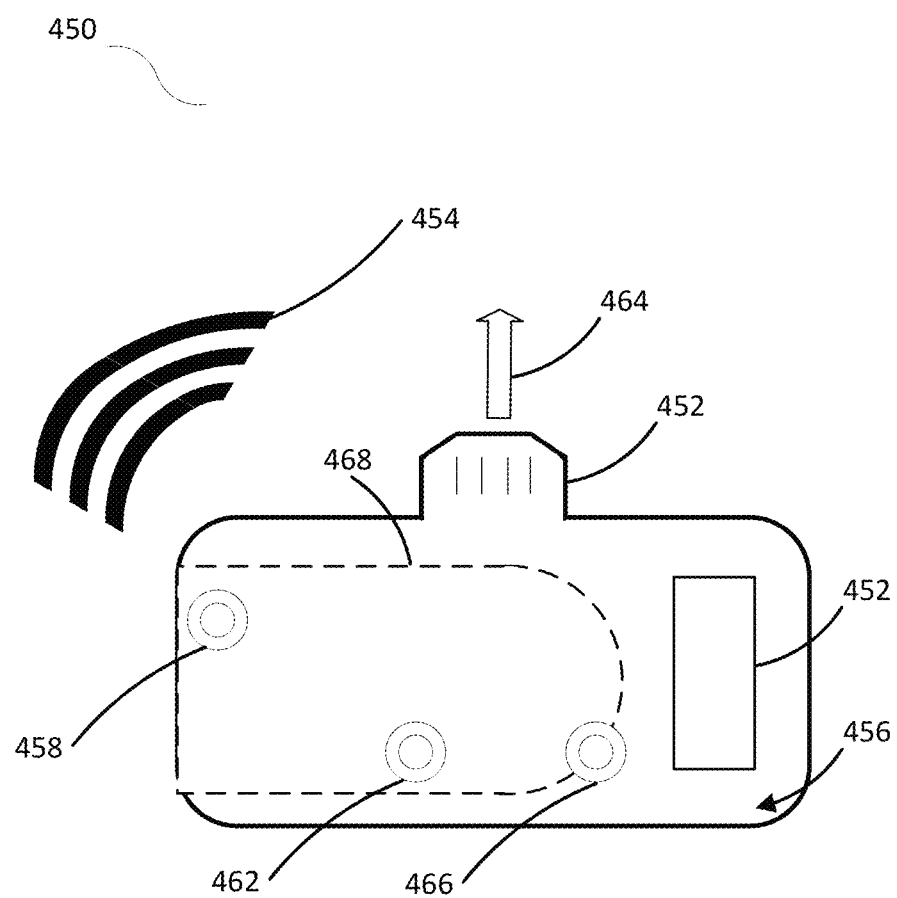

FIG. 4(c) shows a separate, standalone device 450 usable for measuring blood pressure via a cuffless, non-invasive technique as disclosed herein. The device 450 may be an accessory to a mobile device (e.g., a mobile phone or tablet) or other computing device computer, or may be integrated into other equipment or vehicles in which it may be desirable to quickly and noninvasively measure blood pressure (e.g., in a patient bed within an ambulance, where space otherwise given to a cuff system could be utilized for other instruments). As shown, device 450 is configured to electrically connect to a mobile device or computer via a standard physical data connection 452. Data connection 452 may be a Lightning connection, a USB connection, a micro-USB connection, or other similar connection. Rather than physically connecting the accessory device 450 to a mobile device, the accessory device 450 could also connect wirelessly, e.g., through a Bluetooth or WiFi connection 454. Device 450 comprises a primary surface 456, which may include a display screen (such as the screen 418 of a mobile device) or may merely include a strain gauge array. The primary surface 456 may also include a camera 458, similar to the camera 424 of the mobile device 420. However, for accessory device 450, the camera may be a lower-cost, lower resolution camera, or may be configured to detect only red/infrared wavelengths. Camera 458 is positioned such that a finger would be oriented and placed on a long axis 460 of the device. Alternatively, a camera 462 or dedicated photoplethysmography sensor (which includes a dedicated infrared or general light source and photodetector) could be placed such that a finger could be oriented along a short axis 464 of the device 450. Or, as another option, a camera 466 could be placed at any convenient location on primary surface 456 that best aids a user in assessing positioning of her finger. When used, accessory 450 may rely on the screen 418 of the connected mobile device 420 to display results and feedback to the user. Alternatively, the primary surface 456 of the accessory could include a display or LED indicators that show results and feedback to the user. For example, the accessory could display a finger silhouette 468 for positioning purposes as well as a blood pressure readout 470.

Figure 4D:
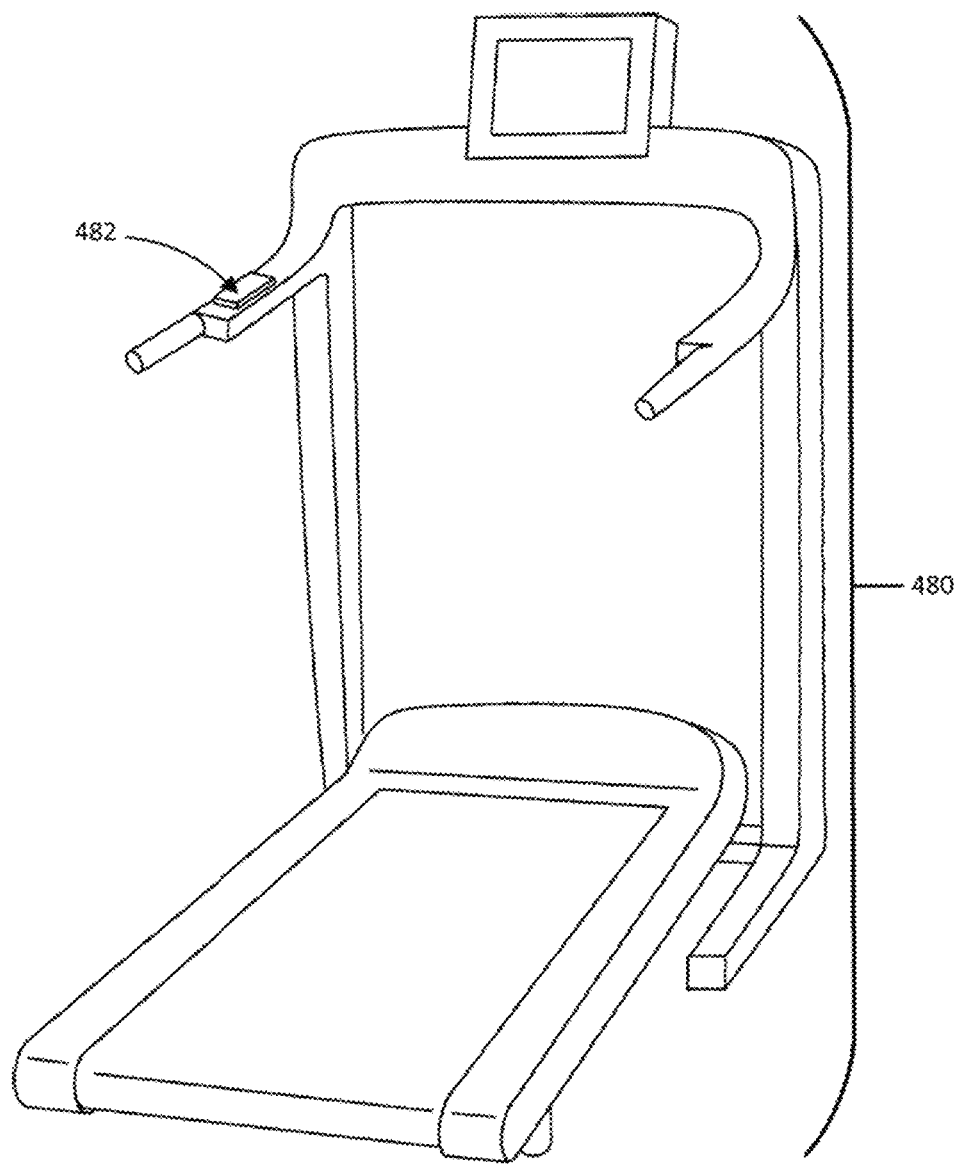

FIG. 4(d) shows how a device as disclosed herein could be integrated into piece of patient care equipment, fitness equipment, or other equipment. As shown, a rehabilitation treadmill 480 is configured to include a finger pressure surface 482, which would include hardware and programming similar to that of the mobile device 420 or accessory 450. The surface 482 could include a display screen and pressure gauge, as described above. The surface 482 could also include light sources of specific wavelengths useful for assessing heart rate or other physiological information (which could also be captured by the camera) relevant to the purpose for which the equipment 480 is used. For example, similar to many "smart" watches, the surface 482, could include LED light sources in addition to one or more cameras, so that simultaneous measurement of heart rate and blood pressure could be achieved.

It is also contemplated that a fingerprint sensor in a mobile device or otherwise could be used to measure the pressing contact area of the finger even at different finger pressures (i.e. the force the user is pressing with). Alternatively, the capacitive sensor array underneath the screen of the device could be used to provide a real-time area measurement as the user presses their finger against the screen. Additionally, infrared cameras could potentially allow for better blood volume oscillation measurement in low signal conditions such as dark skin and low temperatures.

Figure 5:
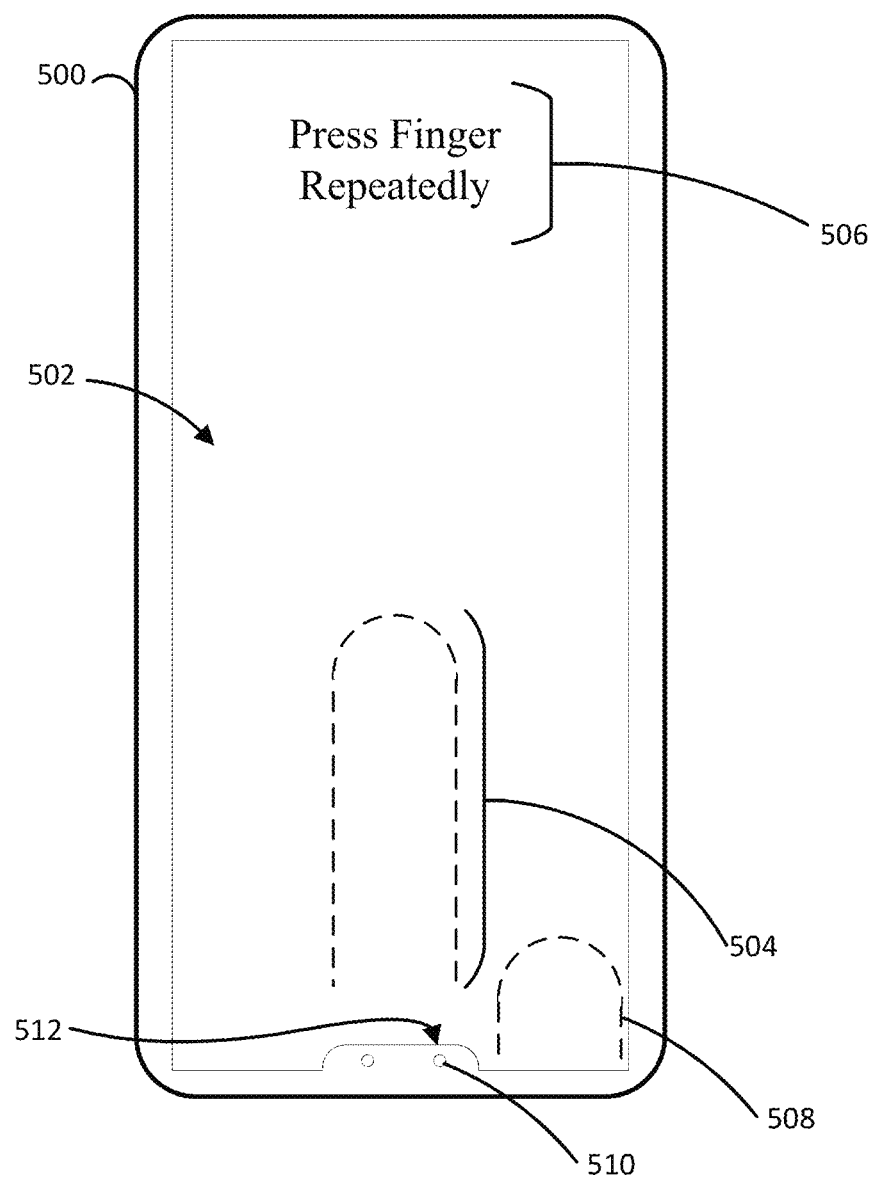
FIG. 5 is a diagram depicting how a user may set up the device of FIG. 4 or other similar embodiments.

FIG. 5 shows a mobile device 500 operating an application for finger-based blood pressure measurement, in a setup or initialization step. The setup or initialization phase may involve measuring the size and profile, or total area, of a user's finger. In an alternative embodiment, an infrared or other sensor could be used to directly detect arterial pattern of a finger. Ultimately, that area can be used with the output of the strain gauge array to compute pressure applied to the artery in a user's finger from which blood pressure is being measured. As shown, the screen 502 is depicting a finger silhouette 504 together with on-screen instructions 506. In this setup phase, the force localization feature of the strain gauge array or localization features of the capacitive touch screen layer (not shown) beneath screen 502 can be used to determine size of a user's finger. In other words, when a user presses her full finger within the silhouette area 504, localized feedback from the strain gauge array, fingerprint scanner, or capacitive touch screen can create a detailed size and profile of a user's finger. In addition, the on-screen instructions 506 can instruct the user to move, remove, repress, roll, tilt, and adjust finger positioning to ensure an accurate measurement. Animations of the required finger movements could also be provided. In one embodiment, the strain gauge array or capacitive touch screen layer can detect the relative distance between the ultimate distal end of the finger and the underside crease of the last or distal knuckle, by detecting the comparative difference in pressure or deflection of the array beneath the crease or the lack of contact between the user's skin and the screen at the location of the crease. Alternatively another anatomical marker (e.g., base of fingernail) could be used in lieu of the location of the crease. In another embodiment, the screen can instruct the user to align the crease beneath their distal knuckle at the edge of the screen 502, e.g., using a different silhouette 508. In yet another embodiment, a user can press her finger on the screen with one hand (so that the strain gauge or capacitive touch sensors can assess finger area), while marking a line with the other hand to indicate where the top knuckle is located.

In yet another embodiment (for example where the strain gauge or capacitive sensors are compromised or not accurate-enough), a user could place her finger on a screen and create a manual outline of her finger, from which finger area can be determined. This could be done by, for example, sliding vertical bars on the screen to the sides of the finger, and sliding a horizontal bar to top of the fingertip, and then marking a horizontal line to indicate where the top knuckle is located. The area inside the box created by the two vertical and two horizontal lines could be taken as a rough measurement of fingertip area. (The same process could also be done to obtain area of the side of a finger, rather than the underside/fingertip side of a finger). Or, in some devices, a user could trace her finger using a stylus. Or, in other embodiments, a user could place her finger on a measurement card (having predetermined markers), next to a coin (or other object of known dimensions) and the user could take a photo of her finger from which programming of the mobile device could assess size. For example, a computer vision application could find the edges of a user's finger to determine a profile, determine the point in the finger at which the crease under the top knuckle occurs, find the edges of a coin or marker in the image, and determine area of the user's finger by comparison to the size of the known dimensions of the coin or marker. This process would only need to be done once per user.

One purpose of this measurement is to develop a customized silhouette for the user's specific finger size, to guide fingertip (or side-of-finger) placement on the screen when measuring BP such that the underlying transverse palmar arch artery (at about the middle of the fingertip) is properly placed above or near the camera. Another purpose is to estimate the finger pressing contact area on the screen, which is used in some embodiments to compute finger pressure as force divided by area for the portion of a user's finger being applied to the screen. This measurement need only be made once per user, as finger dimensions and pressing contact area hardly change throughout adulthood.

In one embodiment, based on a training dataset comprising index fingertip width and height measurements via the application, and reference finger pressing contact area measurements via fingerprinting from 20 subjects, the screen finger pressing contact area (A, mm2) was calculated as $A=0.56 \text{ w}-\text{h}-5.67$, where w and h are specifically the fingertip width at the base of the nail and half the height of the fingertip starting from the crease under the distal knuckle minus the distance from the camera center 510 to the screen edge 512 in the direction of the center of the screen 502 (e.g., 2.7 mm). (Note that the fingerprints were obtained during firm pressing and may thus be valid around the maximum blood volume oscillation regime, which includes mean BP and is mainly used for BP computation.) The program running on the device 500 would need to be customized or customizable to the particular device specifications (the above specifications are specific to an iphone X model), so that the precise distance from the camera center to the screen edge 512 could be known (either supplied from manufacturer specifications or determined empirically). Therefore, in one embodiment, the setup mode would involve confirming with the user the particular device model being used.

Another purpose of the finger measurement at the initialization stage is to determine area (e.g., in mm2) for the portion of the finger that will be pressed on the mobile device screen during a blood pressure measurement. In some mobile devices, the strain gauge array might output only a total detected force value, rather than localized force data. Therefore, to compute pressure on the user's finger during a measurement, total force and total area can be used to compute a value indicative of pressure on the artery of interest.

Finger pressing contact area can be difficult to measure. Some devices provide an estimate of the contact area via a capacitive sensor array, but this measurement may not be of high enough resolution to provide an accurate measurement. When determining blood pressure, an error in finger pressing contact area of 15 mm may correspond to a 10% blood pressure error. For newer devices, a fingerprint scanner under the screen can be used to measure contact area. In older devices, a formula can be determined to predict the finger pressing contact area from the measured fingertip dimensions. In other words, empirical data can be used to predict finger dimensions from a width and height measurement of a finger. Additionally, blood pressure changes effectuated via hand movements can be used to derive area. For example, hand raising maneuvers can be made by a user to change finger BP by a known amount. From this, finger contact area can be derived in lieu of direct measurements, as will be explained below.

Larger contact areas may provide more reliable measurements and easier finger actuation at the expense of less reliable blood volume oscillation measurement and the maximum attainable finger pressure. In an initialization step of an application, an iterative approach can employed where the user puts progressively more of her finger on the screen. Then, the largest screen area that still allows a good PPG and oscillogram can be selected for the finger placement. If the finger pressure saturates during subsequent BP measurements for the user due to too large of an area, then the application can prompt the user to try again with incremental reductions in the area until BP measurements are obtained.

Measuring blood volume oscillations in low signal conditions can be challenging. While front cameras readily permit measurement of the blood volume oscillations by spatial averaging of, typically, a single channel, some cameras do not include a flash, and visible light does not penetrate beneath the skin. As a result, the signal strength is compromised under poor lighting environments and colder settings due to skin vasoconstriction. For certain devices, the front infrared camera and flood illuminator (i.e. flashlight) for "face ID" can be used to penetrate beneath the skin with a dedicated light source and provide more accurate blood volume oscillations measurements. For the older devices, various combinations of the red-green-blue (RGB) channels to mitigate noise can be used to determine blood volume oscillations.

For example, for an iPhone X, the infrared system on the notch can be used as a PPG sensor, and the flood illuminator can be used as a dedicated light source and the adjacent infrared camera can be used as a photodetector. More specifically, the infrared source can be controlled to provide continuous rather than intermittent illumination. Spatial averaging of each frame of infrared video can then be performed, followed by band-pass filtering (e.g., passband from 0.5 to 5 Hz) to extract the blood volume oscillations in relatively low ambient lighting (i.e. at night) or colder environments.

For other smartphones, the RGB channels obtained via the video camera can be combined in order to mitigate noise. Generally, each channel will produce a different pulse amplitude due in part to the wavelength-dependent light absorption characteristics of hemoglobin, but the same noise once the spatially averaged channels are normalized by their mean values. For example, subtracting the pair of channels with the largest and smallest pulses can mitigate the noise more than the signal. Including the third channel can help further. Empirical methods to integrate the RGB channels and a method for non-contact video camera measurement of blood volume oscillations by signal-to-noise ratio maximization can also be used to mitigate noise. Advanced processing of the RGB camera channels can potentially improve waveform quality.

In an iphone X application, the fingertip can be positioned so that the transverse palmar arch artery is directly above the optical/video camera. Such positioning may not be appropriate for earlier smartphones, as they have a significant bezel (i.e., the non-screen portion of the front of the phone) and thus a longer distance between the camera and screen. For example, the distance between the camera and screen edge is just 2.7 mm for the iphone X but about 7.6 mm for earlier iPhones. Hence, placing the artery above the camera on earlier iPhones may not allow enough of the fingertip to be on the screen for reliable finger pressure measurement absent additional measures being taken. Furthermore, for all smartphones, moving the fingertip further on to the screen can improve both finger pressure measurement (i.e., better force registration and greater robustness to fingertip mis-positioning due to the larger finger pressing contact area) and ease of finger actuation (i.e., less pressure sensitivity to modest force variations) and thus usability. Hence, in earlier phones, the transverse palmar arch artery may be placed in between the screen edge and camera.

Alternatively, a side of a finger can be positioned against the screen of the device in order to allow better measurements to be made. A digital artery runs along the side of the finger. Pressing the side of the finger allows a relatively large portion of the finger to be positioned against the screen while still being able to obtain PPG measurements.

For newer mobile devices, the fingerprint can be measured using the optical recognition system under the screen at constant finger forces of increasing magnitude by providing visual guidance (i.e. on-screen prompts) to the user. The fingerprint area at each force can be determined by detecting the contour of the fingerprint and summing the pixels therein. Next, the area-force data can be scaled up for congruence with the fingertip position under the assumption of uniform force application. Lastly, an exponential model can be fit to the scaled area-force data. The exponential model, which may be obtained for each user during an initialization procedure of the application, can then be used to derive the instantaneous area from the measured force during the BP measurement. In this way, BP may be accurately measured even in hypotensive users.

For earlier smartphones, a formula for predicting the finger pressing contact area can be determined from subjects of diverse body sizes. Reference fingerprint and fingertip dimension measurements can be obtained from an application. Other dimension measurements such as the fingertip depth may be used in determining the formula. One or more formulas can then be determined based on multiple regression analysis or an ellipse model to predict the reference finger pressing contact area from the fingertip dimensions and other simple data such as gender and age (which may correlate with fingertip tissue stiffness). A more accurate but less convenient method would be to use a single cuff BP reading to calculate the finger pressing contact area. That is, force data from finger pressing may be obtained from the screen (albeit with an unknown finger area). A separate blood pressure measurement is then made using a cuff-based or other system. Then, a scale factor is determined by equating the app measurement to the cuff BP reading, and finger pressing area can be determined. The scale factor between force and area can then be used henceforth for cuff-less BP measurement.

As another alternative, hand raising maneuvers to measure the finger pressing contact area with smartphones can also be used to achieve better measurement results. When a hand is raised (or lowered), BP in the finger changes by ρgh, where ρ is the known blood density, g is gravity, and h is the vertical height change of the hand raise. The term h can be measured with existing applications based on a video camera, an accelerometer, and/or a gyroscope that may be included in a device such as a smartphone. Mean BP may be computed to within a scale factor equal to the finger pressing contact area from the finger oscillograms obtained with the hand at heart level and another level, and the area scale factor may then be determined so that the difference in the two BP values equals ρgh. More conveniently, BP may be computed to within an area scale factor from the finger oscillogram obtained with the hand at heart level. The blood volume oscillations at a constant force (rather than increasing force) may then be obtained at another hand level; and the area may be determined by scaling the difference in the constant force and the force at which the oscillogram is the same amplitude as the blood volume oscillations so that it equals ρgh. While hand raising may be perceived as less convenient than the other methods by a user, hand raising can measure the area during the BP measurement and may thus be impervious to fingertip mis-positioning.

BP at heart level should be measured. For example, if the mobile device is lower than the heart, the finger BP will be higher than the BP at the heart. BP at heart level can be determined using an accelerometer and/or camera of a device. A reference image can obtained from the camera during the initialization of the application in which the user is explicitly instructed to hold the phone at heart level with back straight and neck bent so that the head is above the phone. An additional method that can be used to ensure that the user is holding the phone horizontally via the built-in accelerometer (i.e., the acceleration should read 0 m/s2 along the long-axis of the phone), which may simplify the method. A conservative method involves comparing the user silhouette obtained via edge detection before each BP measurement with the silhouette likewise obtained from the reference image. If the silhouettes are not similar enough, then the application will prompt the user to reposition the phone. The vertical distance between the phone and heart can be estimated using the camera in order to correct the BP measurement despite the height mis-positioning via a ρgh term. A constant horizontal distance between the phone and user can be assumed for a straightforward vertical distance estimate. A trigonometric model can also be created to estimate the vertical distance without the constant horizontal distance.

Figure 9:
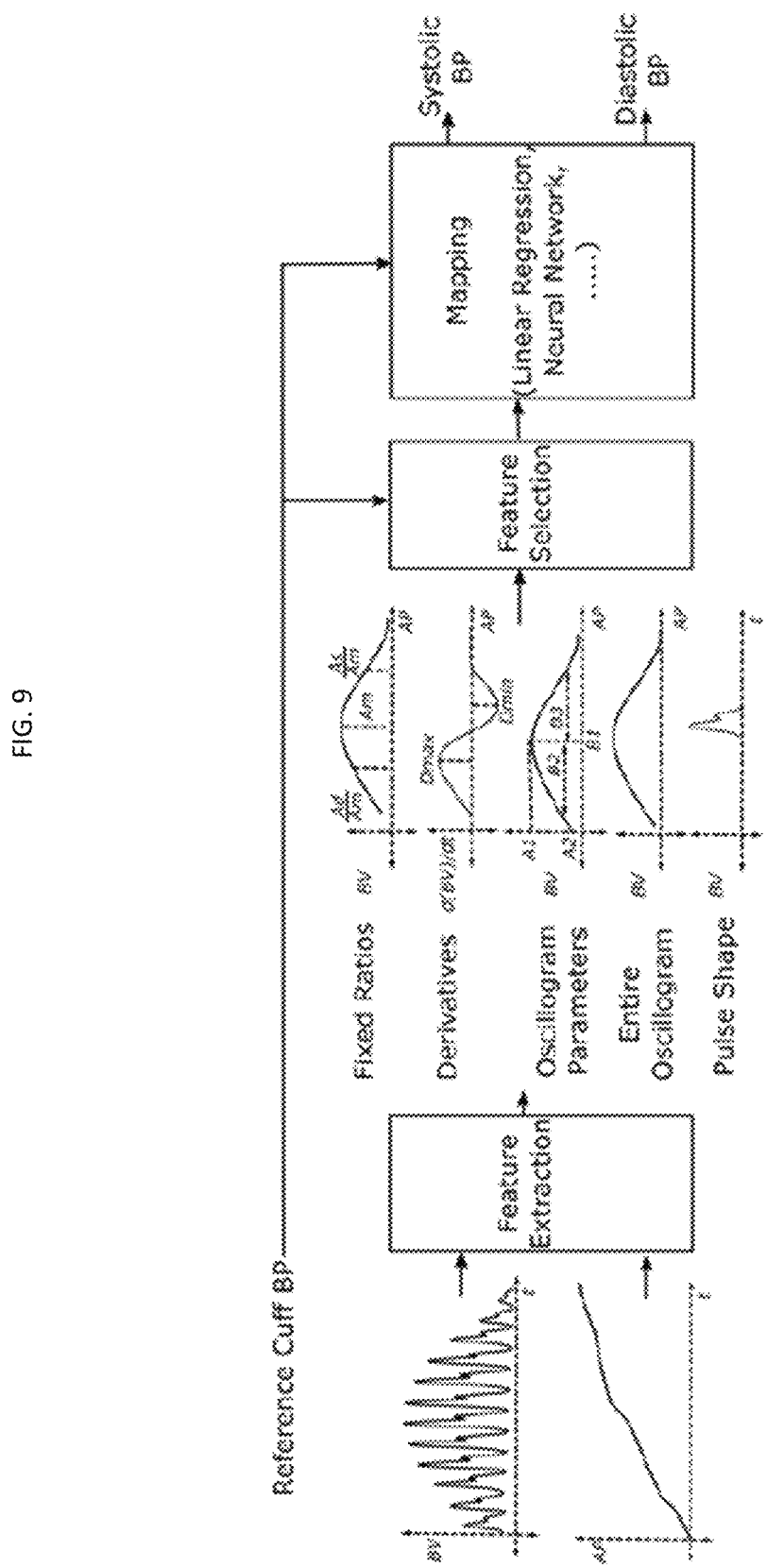
FIG. 9 is an illustrative diagram of a general blood pressure computation process according to some embodiments.

An algorithm for BP computation was derived as follows. (1) feature extraction from the finger blood volume oscillation and pressure measurements; (2) feature selection; and (3) mapping these features to brachial systolic and diastolic BP values. The best features and mapping were determined based on the cuff BP measurements in a training dataset. All data that did not yield physiologic (e.g., concave down and smooth) oscillograms was excluded. Features were derived from the finger oscillograms including fixed ratios, derivatives, other parameters of the oscillogram, and the entire oscillogram itself as well as features from the blood volume pulse shapes. FIG. 9 shows the general process.

Based on fingerprint dimensions from thousands of subjects and the force measurement specifications above, it has been estimated that 95% of people could achieve finger pressure at a maximum of >178 mmHg and resolution of <2 mmHg with the application running on device 500. These specifications are largely congruent with BP measurement.

Figure 6B:
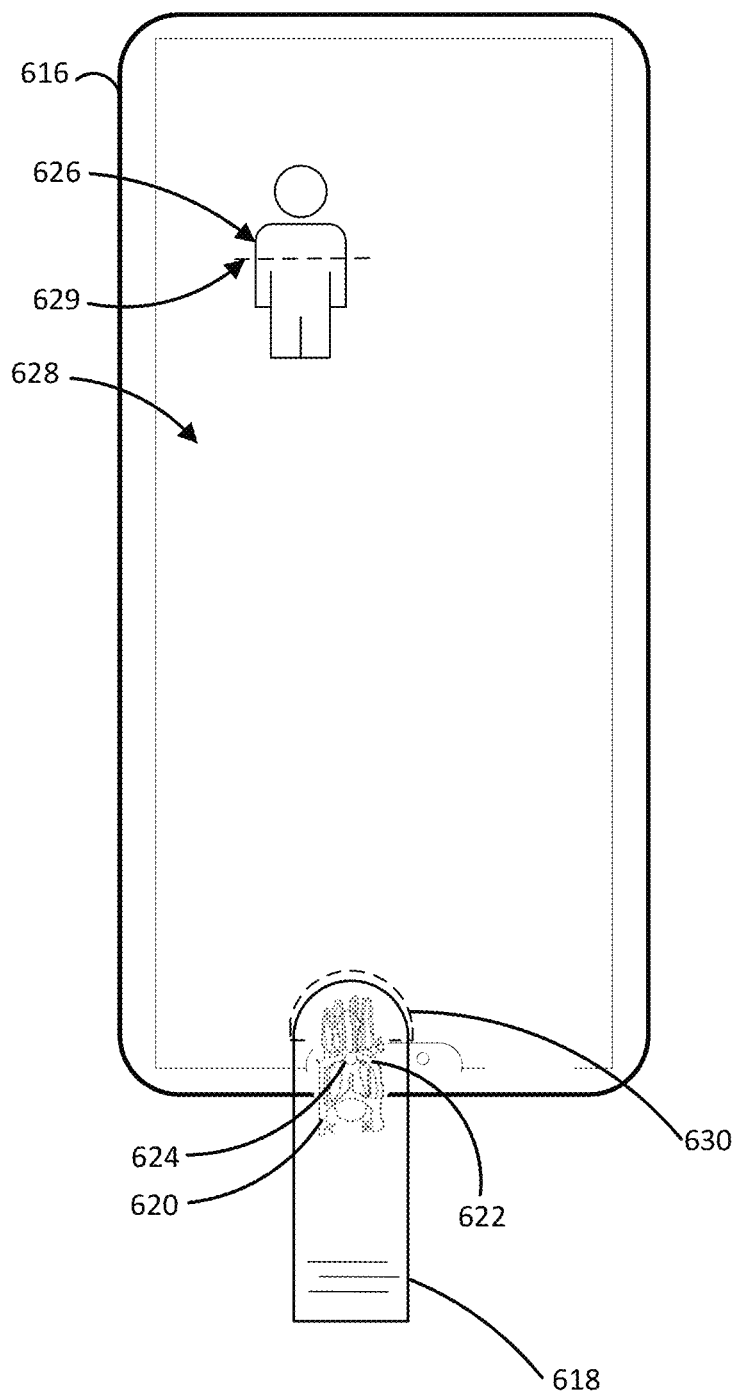
FIG. 6 is a perspective diagram showing a user employing an exemplary device to receive results of the systems and methods herein.
Figure 8A:
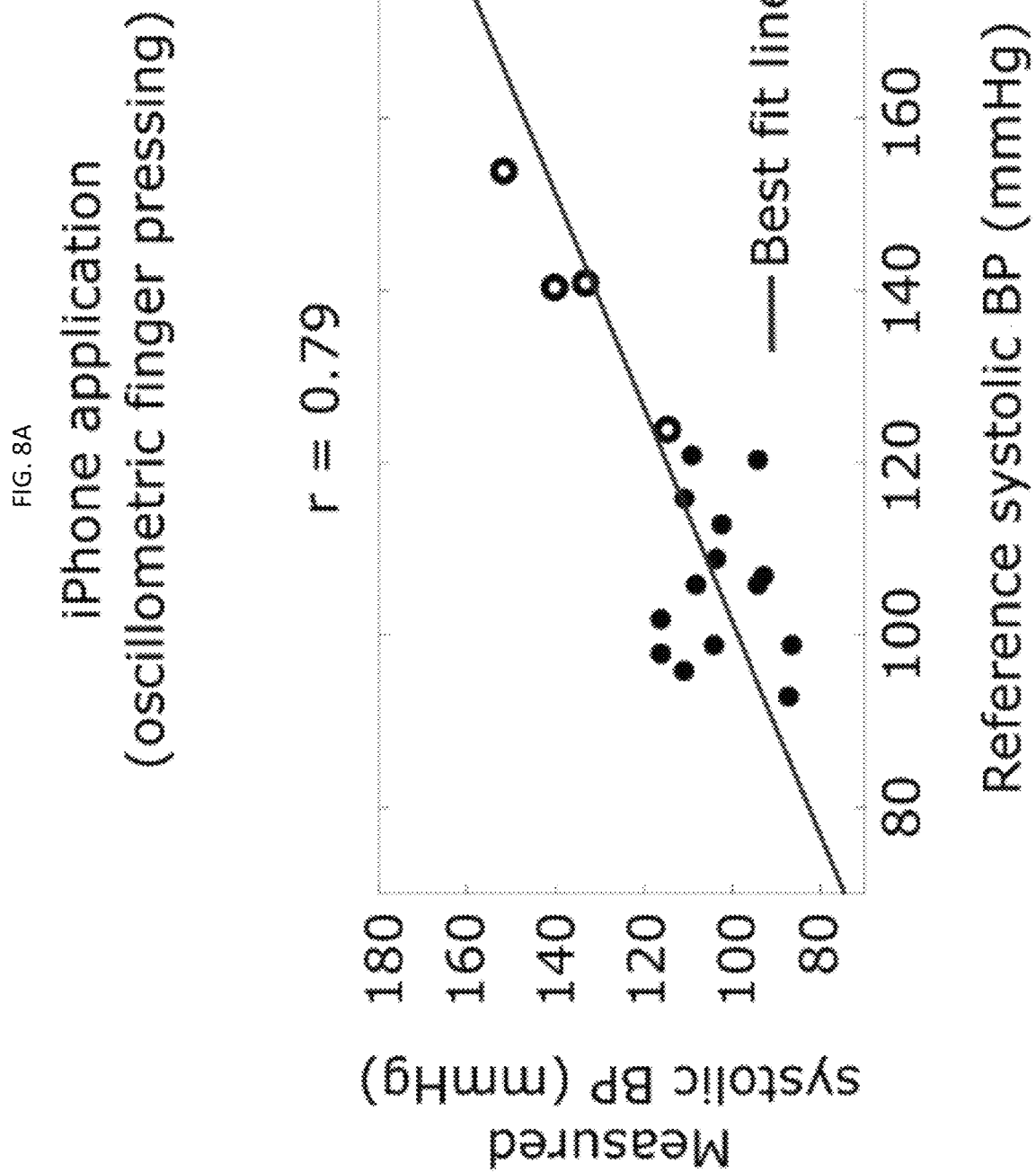
FIG. 8 is a set of correlation and Bland-Altman plots.
Figure 8B:
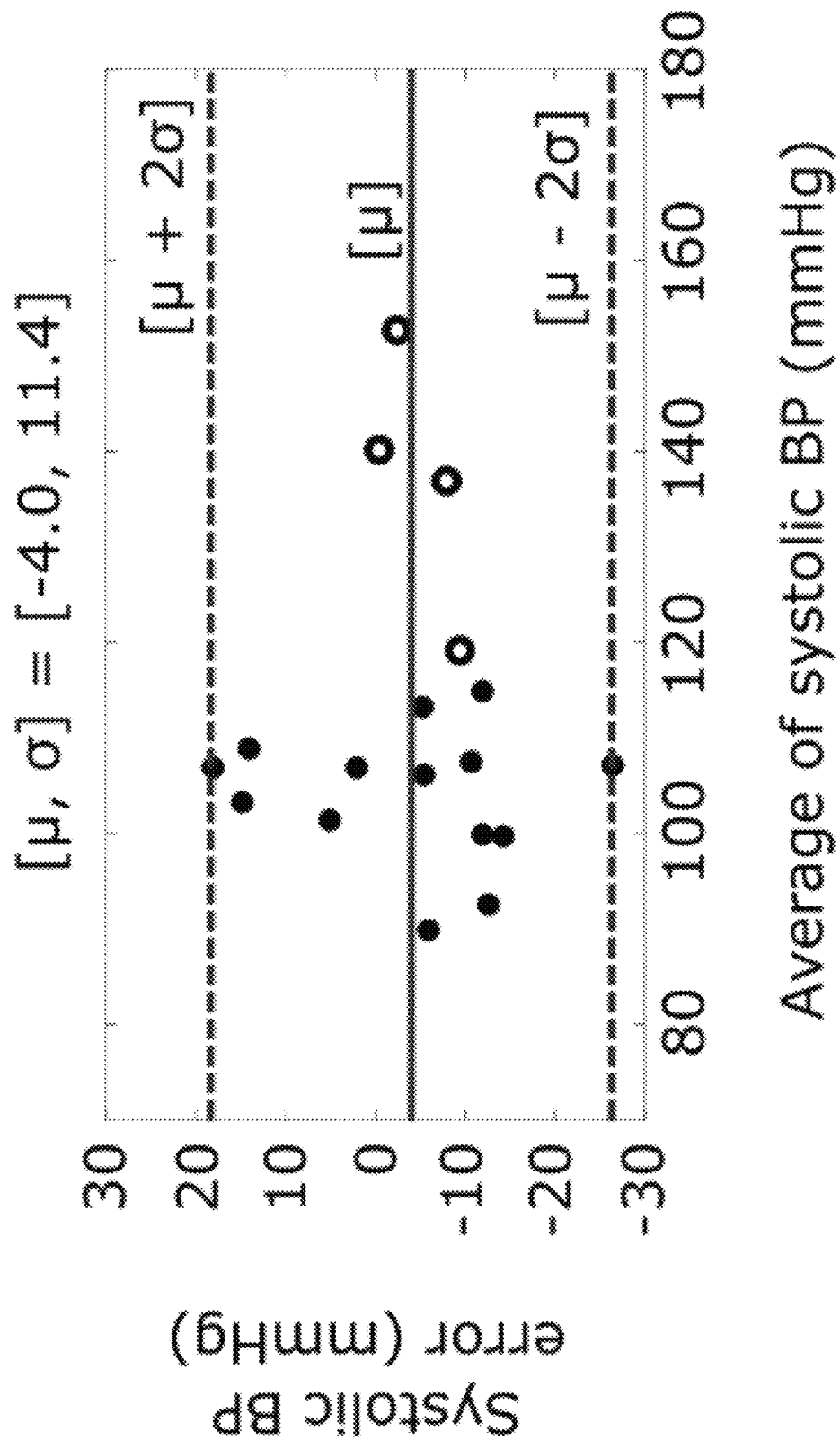
Figure 8C:
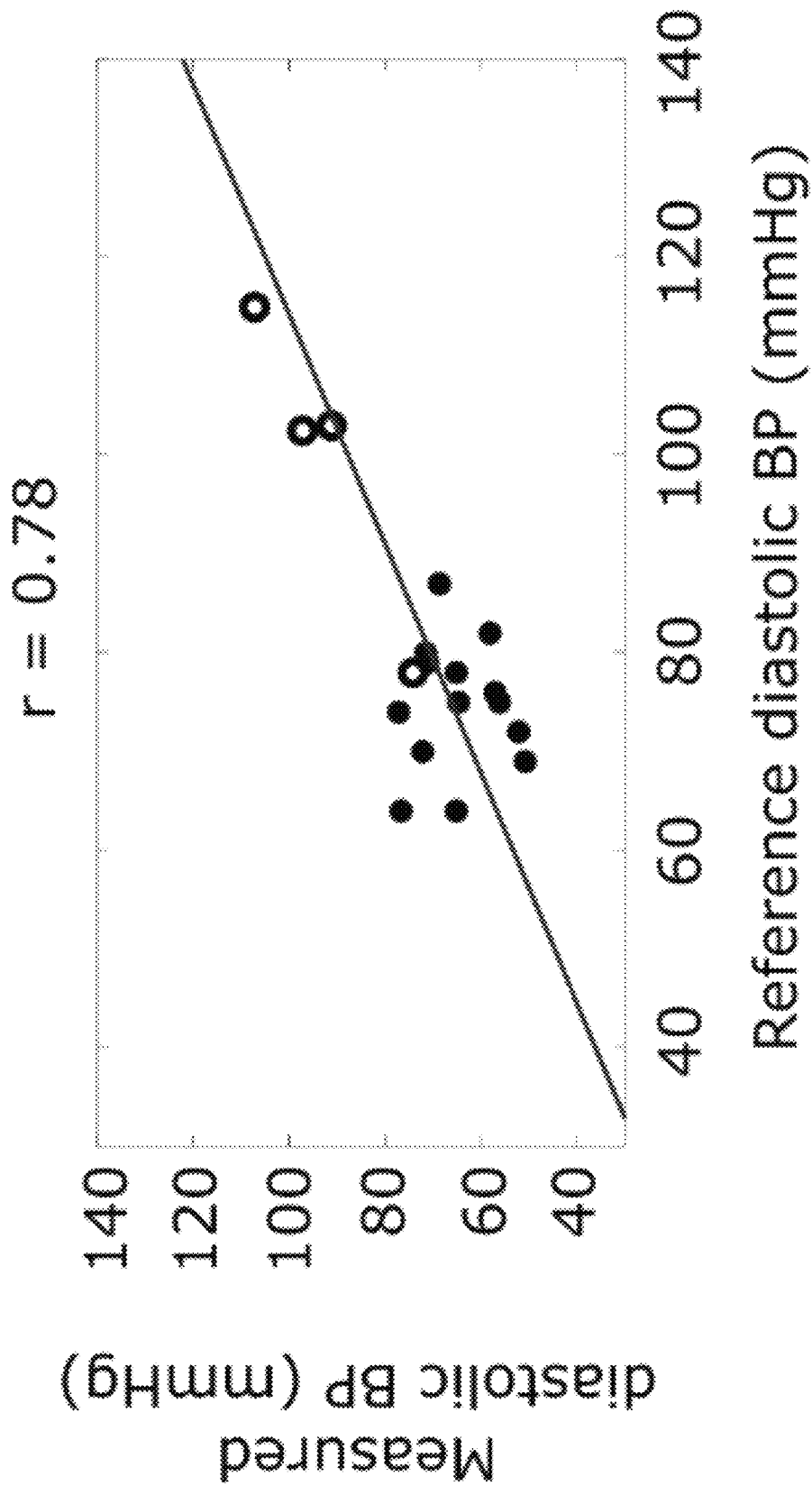
Figure 8D:
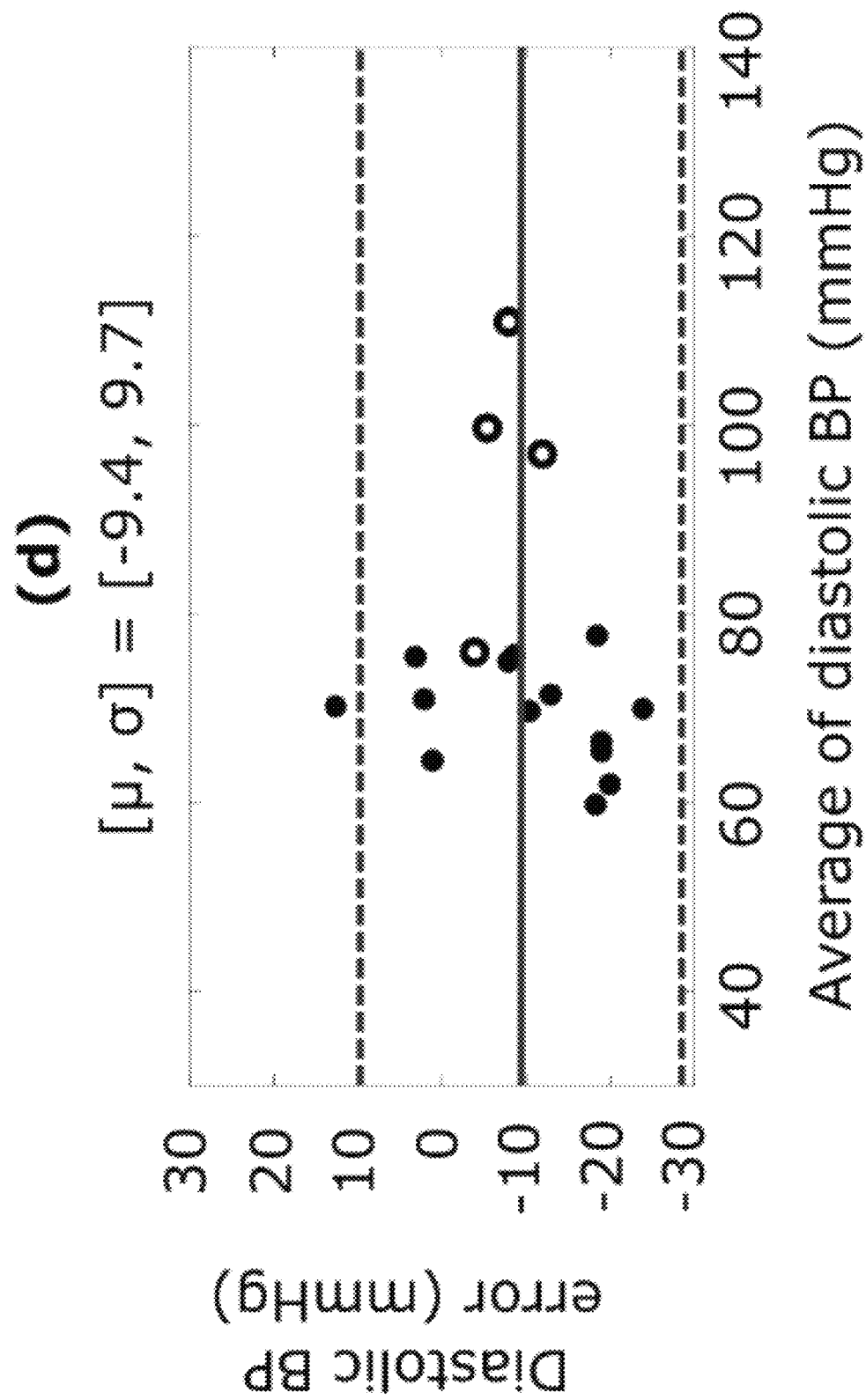

FIG. 6 is a diagram showing the run time use phase of a program running on a mobile device to implement cuffless, calibration-free, finger pressure-based blood pressure measurement. As show in FIG. 6(*a*), a user 600 holds the mobile device 606 in a level, horizontal orientation with one hand. Other orientations are also possible, provided the user attempts to minimize movement so as to minimize the chances of unwanted pressure fluctuations during a measurement. The index finger 602 of the user's other hand is placed fingerprint-side down onto the screen surface 604 of the mobile device. The screen 604 of the device provides a visualization 626 (shown in FIG. 6(*b*)) instructing the user to hold the device 606 in the horizontal orientation within a planar band 629 roughly centered on the user's heart level. In this way, blood pressure is measured at heart level. In one embodiment, the user 600 will have entered in certain biographic health data during the setup phase, such as age, height and weight. The user's height, combined with knowledge of general human anatomical relative positioning, can be used to estimate how high from the floor the device 606 should be held (if a user were standing) or how high from the user's lap the device 606 should be held. That height can be displayed as a suggestion on screen 604. Alternatively, the rear facing camera 612 of the device 606 could be used to estimate height from the floor or user's lap. For example some applications for mobile devices can measure distance 614 from optical output of the rear-facing camera. Based on the optical output of the rear facing camera, the screen 604 could provide a notification to the user 600 to double-check positioning of the device 606 within the target band 608. In an alternative embodiment, if the user holds the device 606 vertically, then prior to the user placing her finger over the camera, the camera could acquire an optical image and assess whether the camera is situated properly in relation to the user's torso (e.g., using arms, shirt pockets, etc. as general markers). Similarly, the internal accelerometer or similar component of device 606 could be used to monitor whether the device is being held level during measurement. For example, if the device 606 were to tilt along any axis while a measurement was being taken, the screen 604 could remind the user to hold the phone steady, to ensure even pressure measurements.

FIG. 6(*b*) shows a top view of the mobile device of FIG. 6(*a*) during a measurement. The user's finger 618 is placed partially over the camera 624 and partially over the screen 628. A partial silhouette 630 of the upper half of a user's fingertip is shown on the screen to help guide the user in placing her finger 618. The size and shape of silhouette 630 may be generated based upon the finger measurement taken during the setup phase, or may be a generic silhouette based on knowledge of average finger dimensions for a user's age, gender, height, and weight. The finger of the user and/or silhouette 630 should be positioned and sized carefully in order to obtain even more accurate BP measurements. The position of the finger on the screen should preferably be chosen based on the distance between the camera 624 and the edge of the screen 628. The size of the finger on the screen 628 grows as the user presses down with increasing force. Larger finger areas on the screen 628 may allow for more reliable pressure measurement and greater ease of finger actuation, while smaller areas on the screen may allow for more reliable PPG measurement. A fingerprint scanners positioned under the screen 628 may also be used to measure finger pressing area on the screen 628.

The arterial network 620 of the user's finger is shown in FIG. 6(*b*) for illustrative purposes. The transverse palmar arch artery 622 is disposed over or near the camera 624 of mobile device 616. Of course, the user will not be able to see her artery 622 or the camera 624 when attempting a blood pressure measurement. Therefore, the silhouette 630 can serve as an important tool to assist the user in ensuring proper finger alignment. In one embodiment, the screen 628 will display real time instructions to the user to move the user's finger toward or away from the center of the screen, or laterally across the camera 624. For example, depending upon the distance from the edge of the device 616 to the camera, and the distance from the camera 616 to the screen 628, the device might display a 'tip' to the user to attempt to place the crease under the top/distal knuckle at the edge of the phone (depending upon the size of the user's finger, the screen may also instruct the user to place the crease past the edge of the phone).

Exemplary Method and Steps of Performing a Blood Pressurement Measurement Using Disclosed Techniques Referring now to FIG. 7, a process flow chart is shown illustrating the steps and logic of a method for measuring blood pressure using the oscillometric principle, without use of a cuff or other such specialized equipment. It is to be understood that the individual steps in this method may be altered in sequence, removed, or replaced as necessary or desirable depending on the equipment and format of the blood pressure measurement modality in accordance with the various embodiments described herein.

The illustrative method 700 begins at step 702 when a user opens the software program or 'app' that implements the method. The user may be presented a welcome screen, with health news or suggestions relevant to the user. At step 704, the method determines if the user has an existing profile or is a new user. For example, the method may require the user to sign in (e.g., via FaceID, TouchID, fingerprint detection, username/password, or merely selecting from a list of known users). If, at step 706, the method determines that there is no valid profile or there were invalid login credentials for the user 708, then the method begins creating a new profile. At step 710, the method acquires basic information about the user, including name, age, height, weight, gender, and the like. Alternatively, the program of the method 700 may be integrated with or connected to an electronic medical record system, such that step 710 includes the user logging in to the EMR system to obtain the user's health data.

At step 712, the method begins the process of measuring the user's finger size and profile. As shown with respect to FIG. 5, this will involve providing visual guidance and instructions to the user for pressing her finger on the screen of the device. At step 714, the method assesses whether a sufficient assessment of the user's index finger has been made. In one embodiment, the method will recursively ask the user to place and re-place her finger on the screen at least a minimum, predetermined number of times. If each measurement is within a set variation, the method may proceed 720. However, if each measurement is not within a statistical congruence 716, then the method may display a request to the user at step 718 to re-press her finger on the screen, and may present further animations or other visualizations to assist the user.

Alternatively, if it is determined at step 706 that a user profile does exist (or if a user profile has been sufficiently created at step 720), then the method proceeds to step 724 at which the method begins assisting the user in proper finger placement for making a blood pressure measurement. At step 724, for example, the method may display alignment visualizations for the user such as shown with respect to FIG. 6(*b*). This may include directional indicators like arrows, or moving or highlighting portions of a finger silhouette in which the user should press her finger. In one embodiment, the camera of the mobile device can process initial image data to determine whether it is detecting arterial blood flow through the transverse palmar arch artery, and then based on such determination the method could guide a user to move her finger up or down, or laterally across the screen. Similarly, the method can also detect the user's finger location by acquiring localized pressure data from a strain gauge of the device's screen.

In addition, step 724 may also involve guiding the user to hold the device at heart level. As discussed with respect to FIG. 6, this may involve written or audio instructions, image depictions, or animations/videos to ensure the user is holding the device at the correct level relative to the user's heart. Step 724 may also entail ensuring the user is holding the device horizontally level. Alternatively, in some embodiments, if the device determines that it was not held precisely at heart level when a measurement was taken, the device can correct the recorded data and measurements for actual heart level rather than asking the user to reposition the device.

The method assesses 726 whether the user is holding the device at the correct height, at a level and horizontal orientation, with her finger in the proper positioning. If not 728, the method provides additional visual or audio feedback to the user until the device and index finger are properly positioned 730.

Next, the method continues by acquiring localized initial pressure data 732 to determine how hard the user is pressing her finger on the device 736. If the user is pressing too lightly or too hard to obtain a valid oscillometric blood pressure reading given the sensitivity of the device's strain gauge array 738, feedback is provided to the user 740. Once the user's finger is at an appropriate baseline pressure 742, oscillometric data acquisition begins at step 744.

Generally speaking, oscillometric blood pressure measuring involves a gradual increase (or decrease) of applied pressure over an artery. For finger pressure-based oscillometry (without use of a cuff or similar equipment), the user is the "actuator." In other words, the user will press her index finger increasingly harder onto the device. To aid a user in doing this, the screen provides a graphical depiction of calculated applied pressure, at step 734. Applied pressure is determined by either a total pressure reading output by the strain gauge array, or in some devices may be determined on a localized basis from localized readings at various points along the strain gauge array's area.

In one embodiment, the graphical depiction of applied pressure can include a typical two axis graph plotting applied pressure in real time, with an overlaid guidance line to help the user understand whether to increase or decrease pressure. At step 734, the device acquires pressure from the strain gauge array while the user slowly presses her finger. During this time, the camera of the device acts as a photoplethysmography (PPG) sensor to detect and measure contemporaneous blood volume oscillations. In an alternative embodiment, a reflectance-mode photo-plethysmography (PPG) sensor is used in lieu of an optical camera to measure blood volume oscillations. In another embodiment, the PPG sensor may be implemented by a simple light emitting diode (or the native screen brightness) cooperatively operating with a photodetector. In other embodiments, the device provides auditory and/or visual cues to guide the finger actuation or even a video game. The measurements must be obtained over a wide enough finger pressure range (e.g., sub-diastolic to supra-systolic BP).

Using the measured varying amplitude blood volume oscillations and the pressure measurements, the method then computes blood pressure related data, such as an oscillogram (i.e., amplitude of blood volume oscillations as a function of applied pressure), at step 754. From the oscillogram, the SP, DP, and MP of the user are determined and presented, for example using a display of the device as shown in FIG. 4(*b*). Blood volume oscillations can be calculated using spatial averaging followed by band-pass (1.8-4.3 Hz) filtering of a red video channel of an optical camera.

In an example embodiment, an oscillogram is constructed by first taking a maximum value and a minimum value of each beat of the blood volume waveform that is detected and measured by the PPG sensor. The maximum value and minimum value of each beat, as a function of the pressure applied to the screen of the mobile device (obtained, e.g., by the output of the strain gauge array), are then median filtered to attenuate respiratory and heart rate variability. Finally, the maximum value and minimum value of each beat are linearly interpolated, and the difference between the two envelopes is taken as the oscillogram. Although not limited thereto, the method may alternatively generate an oscillogram using other known algorithms as would be understood by one having skill in the art, or the method may skip generation of a full oscillogram and instead merely determine systolic and diastolic pressure values.

At step 746, the method assesses the computed results and determines if they are valid. For example, the method may determine if the computed values are within plausible ranges (e.g., are not negative values, or values far above what is possible for a human). If so 752, the values are presented to the user via the screen of the device. If not 748, the data acquisition process repeats and new data is acquired and new results computed. A running average of BP measurements (i.e. the average of the last five BP measurements) can also be calculated and output tin order to mitigate random variability and other factors of the BP measurements.

In one embodiment, if the results are invalid, the device may prompt the user to repeat her finger pressing and/or reposition her finger. If a certain number of subsequent invalid attempts are made using a given finger position (e.g., a position targeting the transverse palmar arch artery over or near the PPG sensor), the device could prompt the user to attempt a different finger position (e.g., a position targeting a digital artery over or near the PPG sensor). This iterative process could continue for multiple arterial locations until valid results are obtained. In one embodiment, an arterial mapping obtained from an infrared or fingerprint scan could be used to predict which arterial locations will present the best chance of acquiring a valid signal. Similarly, once valid results are obtained, the specific finger position that provided the best valid results could be stored in a user setting so that subsequent measurements could start with a prompt for that finger position.

Given that the user is acting as the "actuator" for this acquisition, issues of detecting beats in the presence of artifact, or connecting the extrema of valid beats (which can be separated by a wide range of the pressure applied to the screen, may be present. To overcome these issues, algorithms that first identify artifact in the blood volume waveform that exploit the anticipated blood volume shape and then detect the maxima and minima of the artifact-free beats can be implemented into the system. Advanced filtering and splining algorithms, as well as parametric model (Gaussian functions) fitting, which may be more robust, can be used to connect the extrema of the clean beats.

To assess the validity of the oscillometric data, various features such as the number of artifact-free beats, the applied pressure range over which these beats extend, and the shape, width, and degree of symmetry of the oscillogram may be analyzed to determine the validity of the measurement. An algorithm such as linear discriminant analysis may be implemented to distinguish between valid and invalid oscillograms based on these features.

Finally, after a valid set of blood pressure values has been determined, they may be stored at step 756 for future use. For example, they may be stored to show historical values or may be correlated to different user activity. In one embodiment, the mobile device may output blood pressure measurements to a user's EMR, to a preventative medicine application, to a doctor, or to a commercial application (e.g., anonymously to a group insurance database for rate incentive purposes). In another embodiment, text reminders are sent to users with repeatedly high blood pressure measurements to take their medications. In another embodiment, historical heart rate and blood pressure data could be compiled and stored in a remote server, so that a doctor could access the data and modify dosages or prescriptions according to the data. Or, the doctor could proscribe certain activities that might put an at-risk individual in a blood pressure scenario that is unsafe.

A version of an application implementing the blood pressure measurement system described above was tested using an iPhone X. Blood pressure of 20 different subjects was measured using the iPhone. These users included new users who had not use the application before and four experienced users of the application (i.e. persons who had used a previous blood pressure measuring device). Each new user performed three to six practice trials followed by four measurements. Each experienced user performed two measurements holding the phone well below heart level to raise BP and two normal measurements. The application yielded BP in about half the measurements for the new users and outputted BP in 18 of the users. The application may not yield a BP measurement if the finger pressing is not performed correctly, the oscillation and finger pressure measurements are not deemed of high enough quality, or the BP is invalid. The BP measurements from each new user and experienced user holding the device below the heart were averaged and assessed against BP measurements from a standard arm cuff device. FIG. 8a-d shows correlation and Bland-Altman plots for the systolic and diastolic BP measurements from the 18 users. The bias errors ($\mu$) and precision errors ($\sigma$) of the application were −4.0 and 11.4 mmHg for systolic BP and −9.4 and 9.7 mmHg for diastolic BP over about a 50 mmHg range of BP. The application showed errors that were only about 1-2 mmHg higher on average than a finger cuff device that has been FDA-cleared for measuring brachial BP.

The invention claimed is:

1. A device comprising:
a display screen;
a photoplethysmography sensor;
a processor;
a memory connected to the processor containing a set of instructions which, when executed by the processor, cause the processor to:
display, via the display screen, a first guidance visualization directing placement of a finger on the display screen in a measurement position wherein a first portion of the finger is over the display screen and a second portion of the finger is over the photoplethysmography sensor, the measurement position having a relative location on the display screen that is determined according to (i) a general anatomical distance from a tip of a human finger to an approximate location of at least one artery and (ii) a distance from the photoplethysmography sensor of the device to a proximate edge of the display screen;
prompt a user to press the first portion of the finger on the display screen such that the approximate location of the at least one artery will be disposed over the photoplethysmography sensor;
display, via the display screen, a second guidance visualization directing an increasing amount of pressure to be applied by the first portion of the finger over the display screen;
obtain blood volume oscillation data from the photoplethysmography sensor;
obtain pressure data indicating varying pressure applied by the first portion of the finger over the display screen; and
calculate a blood pressure measurement from the blood volume oscillation data and the pressure data.

2. The device of claim 1 further comprising a pressure sensor integrated with the display screen such that the display screen is a pressure-sensitive display screen, and such that the pressure data is acquired from the first portion of the finger over the display screen.

3. The device of claim 2, wherein the pressure sensor comprises a strain gauge array disposed under an outer surface of the display screen, and wherein the pressure data is determined by the processor from output data of the strain gauge array.

4. The device of claim 3, wherein the device is a handheld consumer mobile device.

5. The device of claim 1, wherein the instructions further cause the processor to determine a size of the first portion of the finger over the display screen.

6. The device of claim 5, wherein the instructions further cause the processor to:
display, via the display screen, a prompt for the finger to be placed on the screen for measurement;
obtain data from a sensor integrated with the display screen, the data indicative of area occupied by the first portion of the finger over the display screen.

7. The device of claim 6, wherein the photoplethysmography sensor is at least one of: an optical camera of the device and an infrared camera.

8. The device of claim 7, wherein the optical camera or the infrared camera is disposed on a surface of the device in-plane with the display screen, and wherein the instructions further cause the processor to:
obtain data indicative of a profile of the finger from a capacitive touch sensor of the display screen by prompting the user to outline the finger when pressed on the display screen;
determine, relative to an anatomical marker of the finger, approximately where an artery of interest would be located within the finger profile; and
determine a size and location of the first guidance visualization such that when the finger is placed on the display screen, the first guidance visualization prompts the user to position the anatomical marker so that the artery of interest will be disposed over the optical camera or the infrared camera.

9. The device of claim 7, wherein the device further comprises a light source for assisting the photoplethysmography sensor to obtain the blood volume oscillation data.

10. The device of claim 7, wherein red-green-blue channels of the optical camera are analyzed to derive blood volume oscillations of the finger.

11. The device of claim 1, wherein the first guidance visualization is determined by measuring dimensions of the finger.

12. The device of claim 11, wherein the display screen further comprises an integrated fingerprint scanner, and wherein the instructions further cause the processor to obtain the measured dimensions of the finger using the fingerprint scanner of the display screen.

13. The device of claim 1, wherein the first guidance visualization depicts a visual guide for a size and location for finger pressing that disposes a digital artery along a side of the finger over the photoplethysmography sensor.

14. A method for obtaining a blood pressure measurement comprising:
prompting a user to hold a mobile device at heart level;
prompting the user to press one of the user's fingers against a location on a display screen of the mobile device, the location on the display screen having a relative position on the display screen based upon a general anatomical distance from a tip of a human finger to an approximate location of at least one artery and a distance from an optical sensor of the mobile device to a proximate edge of the display screen;
acquiring force data indicative of force applied by the user's finger against the display screen;
measuring blood volume oscillations within at least one artery of the user's finger via the optical sensor of the mobile device while the user is pressing the finger on the display screen;
calculating a blood pressure reading based upon the force data and the measured blood volume oscillations; and
displaying the blood pressure reading to the user via the display screen of the mobile device;
wherein the step of prompting the user to press one of the user's fingers against the display screen comprises prompting the user to press a portion of the user's finger on the display screen such that the approximate location of the at least one artery will be disposed over the optical sensor.

15. The method of claim 14 further comprising performing a user initialization comprising obtaining a measurement of dimensions of the portion of the user's finger.

16. The method of claim 15, wherein the measurement of dimensions of the portion of the user's finger is determined by obtaining a cuff-based blood pressure measurement, and a measurement of force applied by the portion of the user's finger against the display screen, and calculating area of the portion of the user's finger based upon the two measurements.

17. The method of claim 14, wherein a measurement of dimensions of the portion of the user's finger pressed against the display screen is acquired while the force data is being acquired.

18. The method of claim 14, further comprising using an output of device sensors of the mobile device to correct the blood pressure reading for deviations due to the user holding the device at a different level from the heart level.

19. The method of claim 14 further comprising: after the user has pressed the finger against the display screen, determining whether the finger has been placed at the location on the display screen, and if not, displaying a prompt to the user indicating how the user should adjust finger location.

20. The method of claim 14, wherein the prompting the user to press one of the user's fingers against the location on the display screen of the mobile device comprises displaying an outline of a portion of a finger on the display screen at the location.

21. The method of claim 20, wherein dimensions of the outline of the portion of the finger are determined based upon a measured size of the user's finger.

22. The method of claim 14 further comprising:
obtaining a measurement of area of the portion of the user's finger pressed against the screen;
obtaining the force data indicative of force applied against the display screen from a sensor array disposed beneath a surface of the display screen;
calculating pressure data from the area measurement and the force data.

23. A system comprising:
a pressure-sensitive user display screen;
an optical sensor;
a processor; and
a memory connected to the processor, having instructions stored thereon which, when executed by the processor, cause the processor to:
retrieve data indicative of a distance from a tip of a user's finger to an approximate location of at least one artery based upon general anatomical data of human fingers;
retrieve data indicative of a distance from the optical sensor to a proximate edge of the display screen;
display, via the pressure-sensitive user display screen, an indication to the user of a finger pressing location on the pressure-sensitive user display screen, the finger pressing location appearing on the display screen at a position such that, when the user presses a portion of the user's finger on the pressure-sensitive user display screen at the finger pressing location, the approximate location of the at least one artery will be disposed over the optical sensor;
display a real time guidance to the user via the pressure-sensitive user display screen to vary pressure of the finger against the pressure-sensitive user display screen;
receive pressure data from the pressure-sensitive user display screen while the user is applying pressure;
receive output data of the optical sensor, and calculate blood volume oscillations from the optical sensor output data;
calculate an oscillogram from the blood volume oscillations and the pressure data; and
display a blood pressure measurement to the user based on the oscillogram.

24. The system of claim 23, wherein displaying the real time guidance to the user comprises displaying an indication of varying target pressure and a real time indication of actual applied pressure.

25. The system of claim 23, wherein the instructions further cause the processor to send the blood pressure measurement and a heart rate measurement obtained from the same optical sensor to a remote server for storage in a health record of the user.

26. The system of claim 23, wherein the pressure-sensitive user display screen comprises a strain gauge array from which the pressure data is generated, disposed coextensively and beneath an outer surface of the pressure-sensitive user display screen and not beneath the optical sensor.

27. The system of claim 23, wherein the pressure-sensitive user display is a touch screen, and wherein the instructions further cause the processor to obtain a customized measurement of a user's finger by prompting the user to provide a finger profile via the touch screen display.

28. The system of claim 23, wherein the instructions further cause the processor to prompt the user to press the user's fingers against the finger pressing location of the pressure-sensitive user display screen within an outline displayed on the pressure-sensitive user display screen at a location such that when the user's finger is placed within the outline, the at least one artery of the finger will be disposed over the optical sensor.

29. A device comprising:
   a display screen;
   an optical sensor;
   a pressure sensor;
   a processor; and
   a memory connected to the processor, having instructions stored thereon which, when executed by the processor, cause the processor to:
   retrieve data indicative of a distance from a tip of a user's finger to an approximate location of at least one artery based upon general anatomical data of human fingers;
   retrieve data indicative of a distance from the optical sensor to a proximate edge of the display screen;
   prompt the user to press a portion of the user's finger against the display screen such that the approximate location of the at least one artery will be disposed over the optical sensor;
   receive pressure data from the pressure sensor pressed by the portion of the user's finger;
   receive output data of the optical sensor, and calculate blood volume oscillations from the optical sensor output data;
   calculate an oscillogram from the blood volume oscillations and the pressure data; and
   display, via display screen, a blood pressure measurement to the user based on the oscillogram.

\* \* \* \* \*